(12) United States Patent
Oshinski

(10) Patent No.: US 11,860,173 B2
(45) Date of Patent: Jan. 2, 2024

(54) HAZARDOUS CONTAMINANT COLLECTION DEVICE WITH INTEGRATED SWAB AND TEST DEVICE

(71) Applicant: Becton, Dickinson and Company, Franklin Lakes, NJ (US)

(72) Inventor: Matthew Oshinski, Oak Ridge, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/655,516

(22) Filed: Mar. 18, 2022

(65) Prior Publication Data

US 2022/0206021 A1    Jun. 30, 2022

Related U.S. Application Data

(63) Continuation of application No. 16/750,343, filed on Jan. 23, 2020, now Pat. No. 11,280,801.
(Continued)

(51) Int. Cl.
*G01N 33/94*    (2006.01)
*B01L 3/00*    (2006.01)
*G01N 1/02*    (2006.01)

(52) U.S. Cl.
CPC ............ *G01N 33/94* (2013.01); *B01L 3/5029* (2013.01); *B01L 3/502776* (2013.01);
(Continued)

(58) Field of Classification Search
CPC .... G01N 33/94; G01N 1/02; G01N 2001/028; B01L 3/502776; B01L 5/5029; B01L 2200/0636; B01L 2300/042
See application file for complete search history.

(56) References Cited

U.S. PATENT DOCUMENTS

| 1,853,238 A | 4/1932 | Shields |
| D229,689 S | 12/1973 | Dragotta |

(Continued)

FOREIGN PATENT DOCUMENTS

| CA | 2708568 A1 | 12/2010 |
| CN | 101052877 A | 10/2007 |

(Continued)

OTHER PUBLICATIONS

Chen et al., "Study on Application of Modified IPEP in Trace DNA Analysis". Chinese J Forensic Med. 2007; 1: 4-7.
(Continued)

*Primary Examiner* — Jennifer Wecker
*Assistant Examiner* — Kathryn Elizabeth Limbaugh
(74) *Attorney, Agent, or Firm* — Knobbe, Martens, Olson & Bear, LLP

(57) ABSTRACT

Contamination detection systems, kits, and techniques are described for testing surfaces for the presence of analytes of interest, including hazardous contaminants, while minimizing user exposure to these contaminants. Even trace amounts of contaminants can be detected. A collection device provides a swab that is simple to use, easy to hold and grip, allows the user to swab large areas of a surface, and keeps the user's hands away from the surface being tested. The collection device also includes a test strip, and provides a closed fluid transfer mechanism to transfer the collected fluid from the swab to the test strip while minimizing user exposure to hazardous contaminants in the collected fluid. Contamination detection kits can rapidly collect and detect hazardous drugs, including trace amounts of antineoplastic agents, in healthcare settings at the site of contamination.

20 Claims, 14 Drawing Sheets

Related U.S. Application Data

(60) Provisional application No. 62/797,804, filed on Jan. 28, 2019.

(52) U.S. Cl.
CPC ........ *G01N 1/02* (2013.01); *B01L 2200/0636* (2013.01); *B01L 2300/042* (2013.01); *G01N 2001/028* (2013.01)

(56) References Cited

U.S. PATENT DOCUMENTS

| | | |
|---|---|---|
| 3,841,973 A | 10/1974 | Wilkins et al. |
| 4,278,437 A | 7/1981 | Haggar |
| 4,353,868 A | 10/1982 | Joslin et al. |
| 4,430,013 A | 2/1984 | Kaufman |
| 4,524,025 A | 6/1985 | Geltosky |
| 4,707,450 A | 11/1987 | Nason |
| 4,724,307 A | 2/1988 | Dutton et al. |
| 4,956,302 A | 9/1990 | Gordon et al. |
| 5,078,968 A | 1/1992 | Nason |
| 5,243,865 A | 9/1993 | Hsu et al. |
| 5,373,748 A | 12/1994 | Lioy et al. |
| 5,422,273 A | 6/1995 | Garrison et al. |
| 5,511,654 A | 4/1996 | de la Rocha |
| 5,511,934 A | 4/1996 | Bracchi et al. |
| 5,543,115 A | 8/1996 | Karakawa |
| D383,851 S | 9/1997 | Wong |
| 5,798,273 A | 8/1998 | Shuler et al. |
| 5,823,592 A | 10/1998 | Kalidindi et al. |
| 5,888,758 A | 3/1999 | Wu et al. |
| 5,902,982 A | 5/1999 | Lappe |
| D425,625 S | 5/2000 | Niermann |
| 6,156,878 A | 12/2000 | Godfrey et al. |
| D438,979 S | 2/2001 | Gomes et al. |
| 6,267,722 B1 | 7/2001 | Anderson et al. |
| 6,382,036 B1 | 5/2002 | Woodmansee |
| 6,464,939 B1 | 10/2002 | Bachand et al. |
| 6,514,773 B1 | 2/2003 | Klein et al. |
| 6,541,269 B1 | 4/2003 | Ramana et al. |
| 6,723,290 B1 | 4/2004 | Wardlaw |
| 6,924,153 B1 | 8/2005 | Boehringer et al. |
| D520,643 S | 5/2006 | Clarke et al. |
| 7,114,403 B2 | 10/2006 | Wu et al. |
| 7,175,993 B2 | 2/2007 | Salamone et al. |
| 7,205,116 B2 | 4/2007 | Salamone et al. |
| 7,276,347 B2 | 10/2007 | Salamone et al. |
| D558,357 S | 12/2007 | Byrd et al. |
| D559,397 S | 1/2008 | Eriksson et al. |
| D560,281 S | 1/2008 | Kozak et al. |
| D574,507 S | 8/2008 | Muir et al. |
| 7,459,281 B2 | 12/2008 | Salamone et al. |
| D594,131 S | 6/2009 | Nguyen |
| 7,837,939 B2 | 11/2010 | Tung et al. |
| D640,795 S | 6/2011 | Jackson et al. |
| 8,076,097 B2 | 12/2011 | Salamone et al. |
| 8,128,871 B2 | 3/2012 | Petruno et al. |
| 8,486,717 B2 | 7/2013 | O'Farrell et al. |
| 8,828,653 B2 | 9/2014 | Zook et al. |
| D743,046 S | 11/2015 | Poll et al. |
| D743,571 S | 11/2015 | Jackson et al. |
| 9,488,585 B2 | 11/2016 | Emeric et al. |
| 9,857,372 B1 | 1/2018 | Pulitzer et al. |
| 9,857,375 B2 | 1/2018 | Konishi et al. |
| D859,683 S | 9/2019 | Harding et al. |
| 10,434,160 B2 | 10/2019 | Dwyer |
| D882,817 S | 4/2020 | Norton et al. |
| D898,220 S | 10/2020 | Esala et al. |
| 10,883,901 B1 | 1/2021 | Henzl et al. |
| D910,200 S | 2/2021 | Reber et al. |
| 10,916,058 B2 | 2/2021 | Isaacson et al. |
| 11,002,642 B2 | 5/2021 | Oshinski et al. |
| D923,195 S | 6/2021 | Harding et al. |
| 11,123,736 B2 | 9/2021 | Mitra et al. |
| 11,125,661 B2 | 9/2021 | Myres, III et al. |
| D933,203 S | 10/2021 | Zhang |
| 11,199,529 B2 | 12/2021 | Harding et al. |
| 11,280,801 B2 | 3/2022 | Oshinski |
| 11,360,001 B2 | 6/2022 | West |
| 11,380,074 B2 | 7/2022 | Isaacson et al. |
| 11,385,146 B2 | 7/2022 | Harding et al. |
| 11,391,748 B2 | 7/2022 | Isaacson et al. |
| 11,413,342 B2 | 8/2022 | Dwyer |
| D976,437 S | 1/2023 | Harding et al. |
| 11,585,733 B2 | 2/2023 | Harding et al. |
| 2001/0034068 A1 | 10/2001 | Spivey et al. |
| 2002/0001539 A1 | 1/2002 | Dicesare et al. |
| 2002/0035869 A1 | 3/2002 | Schroder et al. |
| 2003/0015044 A1 | 1/2003 | Knothe |
| 2003/0086074 A1 | 5/2003 | Braig et al. |
| 2004/0018634 A1 | 1/2004 | Hajizadeh et al. |
| 2004/0248106 A1 | 12/2004 | Leonard et al. |
| 2005/0084842 A1 | 4/2005 | O'Connor |
| 2005/0106753 A1 | 5/2005 | Wu et al. |
| 2005/0136540 A1 | 6/2005 | Quine et al. |
| 2005/0136553 A1 | 6/2005 | Kaylor et al. |
| 2005/0181517 A1 | 8/2005 | Chandler et al. |
| 2005/0187733 A1 | 8/2005 | Staab |
| 2005/0250141 A1 | 11/2005 | Lambert et al. |
| 2006/0074347 A1 | 4/2006 | Eguchi et al. |
| 2006/0089333 A1 | 4/2006 | Morgan |
| 2006/0115805 A1 | 6/2006 | Hansen et al. |
| 2006/0216196 A1 | 9/2006 | Satoh et al. |
| 2006/0246601 A1 | 11/2006 | Song et al. |
| 2007/0137319 A1 | 6/2007 | Nacson et al. |
| 2007/0231923 A1 | 10/2007 | Cumberland et al. |
| 2007/0244368 A1 | 10/2007 | Bayliff et al. |
| 2007/0276786 A1 | 11/2007 | Piedmonte |
| 2008/0081341 A1 | 4/2008 | Maher et al. |
| 2008/0109098 A1 | 5/2008 | Moshier et al. |
| 2008/0118397 A1 | 5/2008 | Slowey et al. |
| 2008/0204221 A1 | 8/2008 | Elderkin et al. |
| 2009/0015273 A1 | 1/2009 | Gossen et al. |
| 2009/0061534 A1 | 3/2009 | Sharrock |
| 2009/0117536 A1 | 5/2009 | Mattey et al. |
| 2009/0223635 A1 | 9/2009 | Lawless |
| 2010/0077843 A1 | 4/2010 | Doraisamy et al. |
| 2010/0267049 A1 | 10/2010 | Rutter et al. |
| 2011/0029252 A1 | 2/2011 | Beaty |
| 2011/0117025 A1 | 5/2011 | Dacosta et al. |
| 2011/0189063 A1 | 8/2011 | Momiyama et al. |
| 2011/0201099 A1 | 8/2011 | Anderson et al. |
| 2011/0269706 A1 | 11/2011 | Chen et al. |
| 2011/0295620 A1 | 12/2011 | Loscalzo et al. |
| 2012/0011944 A1 | 1/2012 | Maughan et al. |
| 2012/0044264 A1 | 2/2012 | Lee et al. |
| 2012/0107956 A1 | 5/2012 | Boehringer et al. |
| 2012/0148611 A1 | 6/2012 | Brodsky et al. |
| 2012/0220043 A1 | 8/2012 | Sangha |
| 2012/0264229 A1 | 10/2012 | Wan |
| 2012/0282154 A1 | 11/2012 | Slowey et al. |
| 2013/0203627 A1 | 8/2013 | Moll et al. |
| 2013/0253295 A1 | 9/2013 | Tolosa et al. |
| 2013/0280143 A1 | 10/2013 | Zucchelli et al. |
| 2014/0017812 A1 | 1/2014 | Smith et al. |
| 2014/0080129 A1 | 3/2014 | Klunder et al. |
| 2014/0121487 A1 | 5/2014 | Faybishenko et al. |
| 2014/0176603 A1 | 6/2014 | Kumar et al. |
| 2014/0183256 A1 | 7/2014 | Calio et al. |
| 2014/0210857 A1 | 7/2014 | Liu et al. |
| 2014/0227796 A1 | 8/2014 | Gold et al. |
| 2014/0309556 A1 | 10/2014 | Fletcher et al. |
| 2015/0072362 A1 | 3/2015 | Lui et al. |
| 2015/0132795 A1 | 5/2015 | Griswold et al. |
| 2015/0211987 A1 | 7/2015 | Burg et al. |
| 2015/0241358 A1 | 8/2015 | Burg et al. |
| 2015/0302662 A1 | 10/2015 | Miller |
| 2015/0323461 A1 | 11/2015 | Chan et al. |
| 2015/0377746 A1 | 12/2015 | Mineo |
| 2016/0019716 A1 | 1/2016 | Huang et al. |
| 2016/0033465 A1 | 2/2016 | Schreiber et al. |
| 2016/0041167 A1 | 2/2016 | Campbell et al. |
| 2016/0057413 A1 | 2/2016 | Zhou et al. |
| 2016/0077013 A1 | 3/2016 | Attar et al. |

(56) References Cited

U.S. PATENT DOCUMENTS

| | | |
|---|---|---|
| 2016/0078680 A1 | 3/2016 | Reif et al. |
| 2016/0258874 A1 | 9/2016 | Truex |
| 2016/0313323 A1 | 10/2016 | Jakubowicz |
| 2017/0016045 A1 | 1/2017 | McDaniel |
| 2017/0036205 A1 | 2/2017 | Bishop et al. |
| 2017/0072393 A1 | 3/2017 | Jackson et al. |
| 2017/0153185 A1 | 6/2017 | Kisner et al. |
| 2017/0154438 A1 | 6/2017 | Kisner et al. |
| 2017/0164802 A1 | 6/2017 | Cudzilo |
| 2017/0182492 A1 | 6/2017 | Liu |
| 2017/0184585 A1 | 6/2017 | Markovsky et al. |
| 2018/0247024 A1 | 8/2018 | Divine et al. |
| 2018/0259429 A1 | 9/2018 | Adams |
| 2018/0293350 A1 | 10/2018 | Dimov et al. |
| 2018/0326031 A1 | 11/2018 | Dwyer |
| 2018/0372595 A1 | 12/2018 | Pais et al. |
| 2019/0035153 A1 | 1/2019 | Dange |
| 2019/0086295 A1 | 3/2019 | Oshinski et al. |
| 2019/0086296 A1 | 3/2019 | West |
| 2019/0086305 A1 | 3/2019 | Harding et al. |
| 2019/0086431 A1 | 3/2019 | Isaacson et al. |
| 2019/0120727 A1 | 4/2019 | Harding et al. |
| 2019/0376966 A1 | 12/2019 | Pulitzer et al. |
| 2020/0298240 A1 | 9/2020 | Oshinski et al. |
| 2020/0393451 A1 | 12/2020 | Sandmann et al. |
| 2021/0192850 A1 | 6/2021 | Isaacson et al. |
| 2021/0255066 A1 | 8/2021 | Oshinski et al. |
| 2022/0099648 A1 | 3/2022 | Harding et al. |
| 2022/0349907 A1 | 11/2022 | Isaacson et al. |
| 2022/0397499 A1 | 12/2022 | Harding et al. |
| 2023/0165947 A1 | 6/2023 | Dwyer |
| 2023/0204464 A1 | 6/2023 | Harding et al. |

FOREIGN PATENT DOCUMENTS

| | | |
|---|---|---|
| CN | 101082051 A | 12/2007 |
| CN | 101087800 A1 | 12/2007 |
| CN | 101326440 A | 12/2008 |
| CN | 101413941 A | 4/2009 |
| CN | 102016062 A | 4/2011 |
| CN | 103033613 A | 4/2013 |
| CN | 104819865 A | 8/2015 |
| CN | 105683751 A | 6/2016 |
| CN | 107102103 A | 8/2017 |
| EP | 0098179 A2 | 1/1984 |
| GB | 2501179 | 5/2013 |
| GB | 2544133 A | 5/2017 |
| JP | S61112984 A | 5/1986 |
| JP | H02163689 A | 6/1990 |
| JP | H02269969 A | 11/1990 |
| JP | 2002502045 A | 1/2002 |
| JP | 2002053816 A | 2/2002 |
| JP | 2002504684 A | 2/2002 |
| JP | 2006284279 A | 10/2006 |
| JP | 2007212391 A | 8/2007 |
| JP | 2008535480 A | 9/2008 |
| JP | 2011158279 A | 8/2011 |
| JP | 2012524277 A | 10/2012 |
| JP | 2016045027 A | 4/2016 |
| JP | 2016050911 A | 4/2016 |
| JP | 2016539338 A | 12/2016 |
| WO | WO 1991/017271 | 11/1991 |
| WO | WO 1992/001047 | 1/1992 |
| WO | WO 1995/25948 | 9/1995 |
| WO | WO 1997/022614 | 6/1997 |
| WO | WO 2000/052015 | 9/2000 |
| WO | WO 2003/001964 | 1/2003 |
| WO | WO 2005042770 | 5/2005 |
| WO | WO 2005/068969 | 7/2005 |
| WO | WO 2006/020263 | 2/2006 |
| WO | WO 2009/018473 | 2/2009 |
| WO | WO 2010/001296 | 1/2010 |
| WO | WO 2010/002883 | 1/2010 |
| WO | WO 2010/085377 | 7/2010 |
| WO | WO 2011/095599 | 8/2011 |
| WO | WO 2013/036913 | 3/2013 |
| WO | WO 2014/001967 | 1/2014 |
| WO | WO 2014/015076 | 1/2014 |
| WO | WO 2014/025415 | 2/2014 |
| WO | WO 2014/202791 | 12/2014 |
| WO | WO 2015/187335 | 12/2015 |
| WO | WO 2016/040642 | 3/2016 |
| WO | WO 2016/078919 | 5/2016 |
| WO | WO 2016/090176 | 6/2016 |
| WO | WO 2017/019598 | 2/2017 |
| WO | WO 2017/151642 | 9/2017 |
| WO | WO 2017/222833 | 12/2017 |
| WO | WO 2018/057801 | 3/2018 |
| WO | WO 2019/060269 | 3/2019 |

OTHER PUBLICATIONS

Chu et al., "Pilot Assessment of the Antineoplastic Drug Contamination Levels in British Columbian Hospitals Pre- and Post-cleaning". J Oncol Pharm Practice Mar. 2012; 18(1): 46-51.

Becton Dickinson—"Detect harmful surface contamination in Minutes", Jan. 31, 2019, 6 pages; retrieved from the Internet: URL: https://www.bd.com/documents/brochures/hazardous-drug-safety/HDS_Check_System_Pharmacy_BR_EN.pdf. [retrieved on Oct. 16, 2022].

Cudzilo M., "AR-Check, Revolutionary Augmented Reality Cleaning System", May 20, 2017, 19 pages; retrieved from the Internet: URL: https://web.archive.org/web/20170520215111/http://ar-check.com/#.

Becton Dickinson—Veritor™ System—for Rapid Detection of Respiratory Syncytial Virus (RSV), Aug. 2017, Retrieved from the internet: <URL: https://www.bd.com/en-us/offerings/capabilities/microbiology-solutions/point-of-care-testing/veritor-system> in 16 pages.

Becton Dickinson—BD Diagnostics Preanalytical Systems—Product Catalogue 2014-15; 2013, Retrieved from internet: <URL:https://www.bd.com/be/dutch/pdfs/PAS_BNL_Prod_Cat_2014_2015_LR_Full_Catalogue.pdf> in 31 pages.

Becton Dickinson—BD HD Check Analyzer—Nursing Brochure; Mar. 2018, in 8 pages.

Becton Dickinson—BD HD Check Analyzer—Pharmacy Brochure; Mar. 2018, in 6 pages.

Chemoglo, LLC, "ChemoGlo™—Detecting and Removing Hazardous Drugs"; available for download at https://web.archive.org/web/20150801115335/http://chemoglo.com/ at least as early as Aug. 1, 2015; 1 page.

Chemoglo, LLC, ChemoGlo™ User Manual; available for download at https://web.archive.org/web/20150801115335/http://chemoglo.com/ at least as early as Aug. 1, 2015; 11 pages.

De Keuckelaere et al., "Semi-Direct Lysis of Swabs and Evaluation of Their Efficiencies to Recover Human Noroviruses GI and GII from Surfaces", Food Environ Virol. (Jun. 2014) 6(2): 132-139.

Henderson S.J., "Augmented Reality Interfaces for Procedural Tasks", Doctoral Thesis; Columbia University, Apr. 14, 2011, 82 pages.

National Infection Service (England), Detection and enumeration of bacteria in swabs and other environmental samples. National Infection Service Food Water and Environmental Microbiology Standard Method, Sep. 1, 2017; 22 pages.

Preprocess, Inc., Sampling and Analytical Technique Considerations for Microbial Surface Swab Testing. 2015; Retrieved from the internet: <URL:http://www.preprocessinc.com/files/documents/d5840edf837f077be7b12e53494ed5b8.pdf> in 3 pages.

Technical Service Consultants Ltd., TS/15-T Product Specification Sheet; Issue #5 of Jun. 6, 2016; Retrieved from the Internet: URL: <http://www.tscswabs.co.uk/uploads/images/product-pdfs/product_specification/spec_TS15-T.pdf> in 20 pages.

International Search Report and Written Opinion dated Apr. 14, 2020 for International Application No. PCT/US2020/014738.

Abbott Diagnostics, "Learning Guide Series Clinical Chemistry", Jun. 14, 2017 (Jun. 14, 2017), XP055727631, Retrieved from the

(56) References Cited

OTHER PUBLICATIONS

Internet: URL:https://www.corelaboratory.abbott/sal/learningGuide/ADD-00061345ClinChem_Learning_Guide.pdf [retrieved on Sep. 4, 2020] in 117 pages.

Bakke et al., Metabolism of Atrazine and 2-Hydroxyatrazine by the Rat, Journal of Agricultural and Food Chemistry, Bates P.K. [Ed.], (1972) 20(2):602-607.

Binotto et al., Ifosfamide and Cyclophosphamide: effects on immunosurveillance. Oncology (2003) 65(Suppl 2):17-20.

Chothia et al., (1987), Canonical Structures for the Hypervariable Regions of Immunoglobulins, J Mol Biol. 196:901-917.

Cox et al., The Use of Cyclophosphamide analogs in mechanistic studies of the metabolism of cyclophosphamide, Proceedings of the 2nd Inter'l Symposium on Mass Spectrometry in Biochemistry and Medicine, Mario Negri Institute for Pharmacological Research, Jun. 1974; Spectrum Publications (1976) 1:59-71.

Harlow et al., [Eds.] Antibodies, A Laboratory Manual Second Edition (C.S.H.P. NY, 2014); Table of Contents in 22 pages.

Huse et al., (1989) Generation of a Large Combinatorial Library of the Immunoglobulin Repertoire in Phage Lambda, Science 246:1275-1281.

Kabat et al., [Eds.] Sequences of Proteins of Immunological Interest, U.S. Department of Health and Human Services; 5th Edition, (1991) in two Volumes; Table of Contents in 28 pages.

Ludeman et al., The Chemistry of the Metabolites of cyclophosphamide. Curr Pharm Des. (1999) 5(8):627-643.

Opheim et al., Particle-Enhanced Turbidimetric Inhibition Immunoassay for Theophylline Evaluated with the Du Pont aca, Clin Chem. Jan. 1984;30(11): 1870-1874.

Paul, [Eds.], Fundamental Immunology (Raven Press, 2d ed., 1989); Table of Contents in 6 pages.

Roitt et al., [Eds.] Immunology (2d ed. 1989), Chapter 6 in 14 pages.

Zhang Y., Effect of Cyclophosphamide on The Immune System, J Anhui Agricultural Sciences, (Dec. 2013) 41(30):12040-12042.

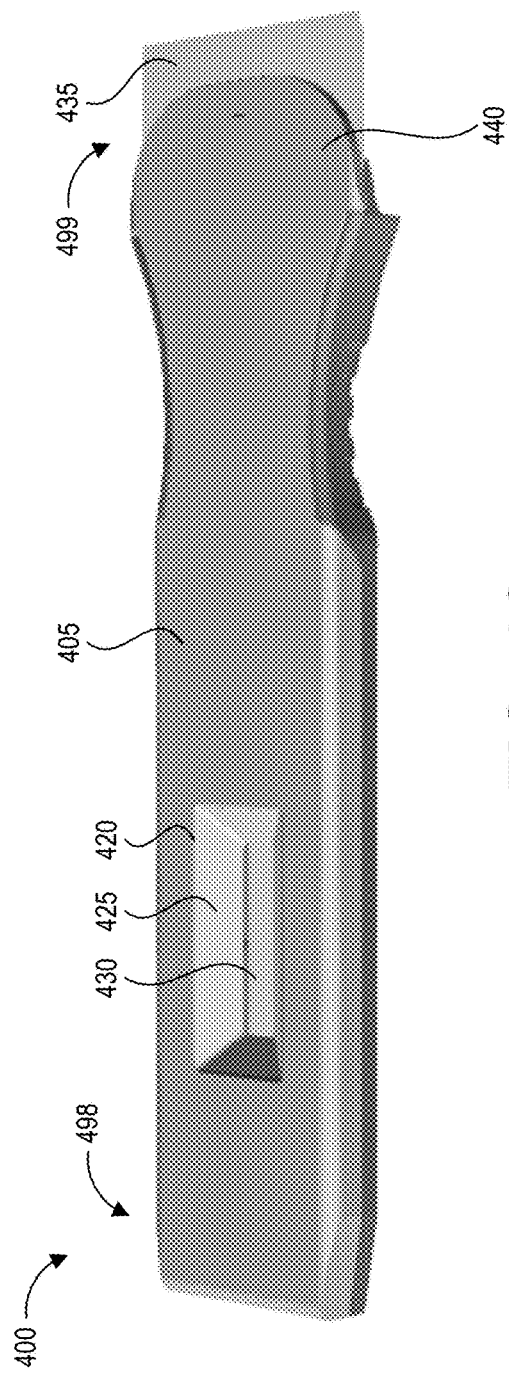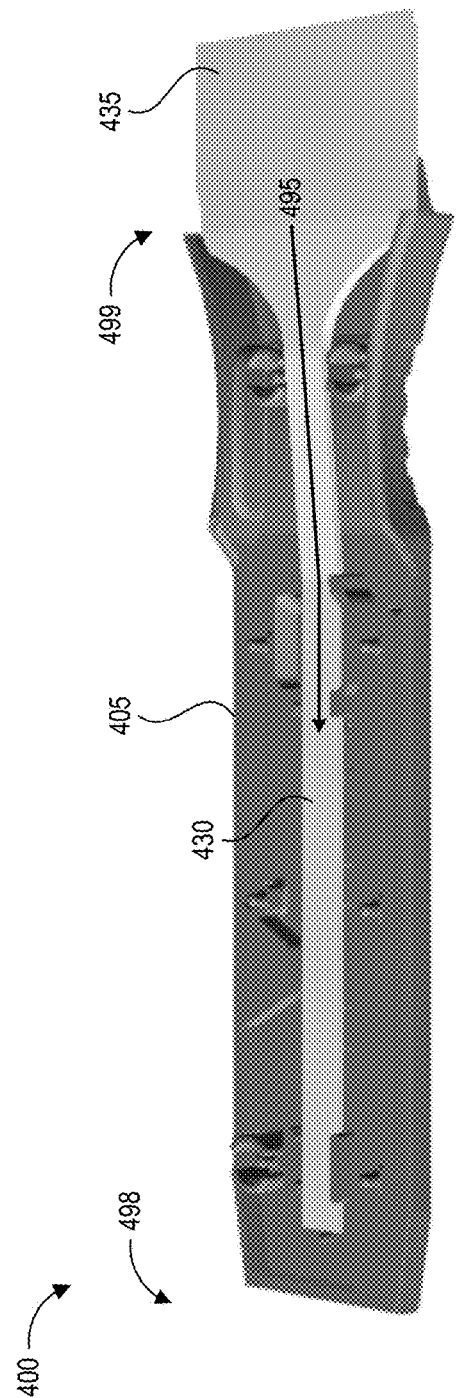
FIG. 4C
FIG. 4D

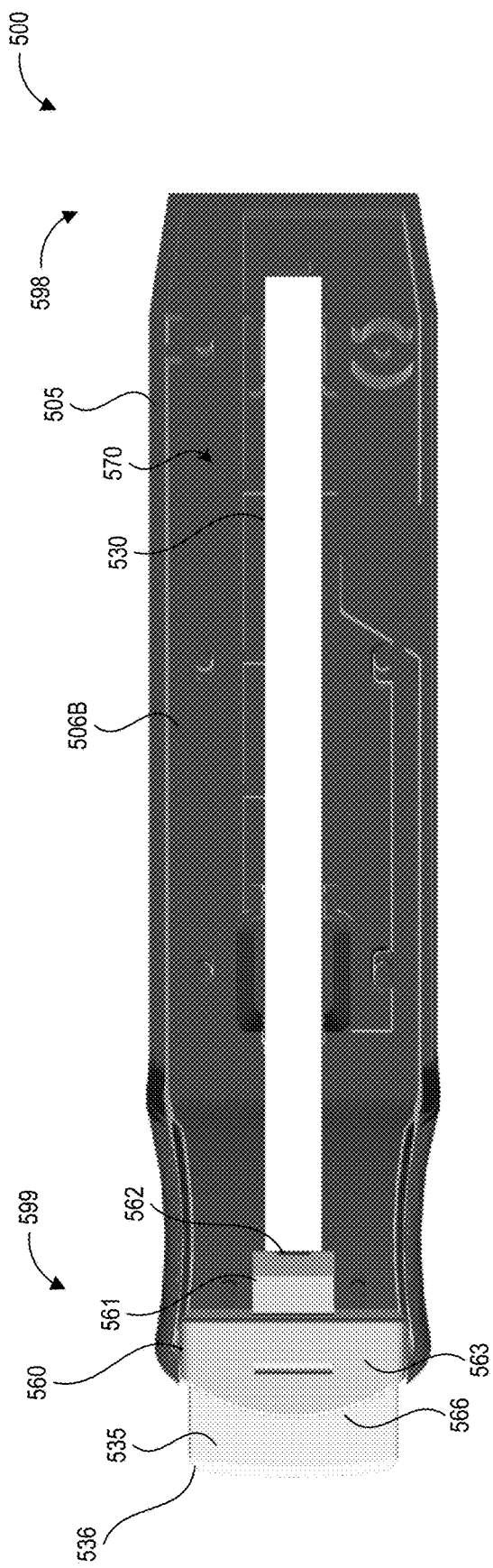
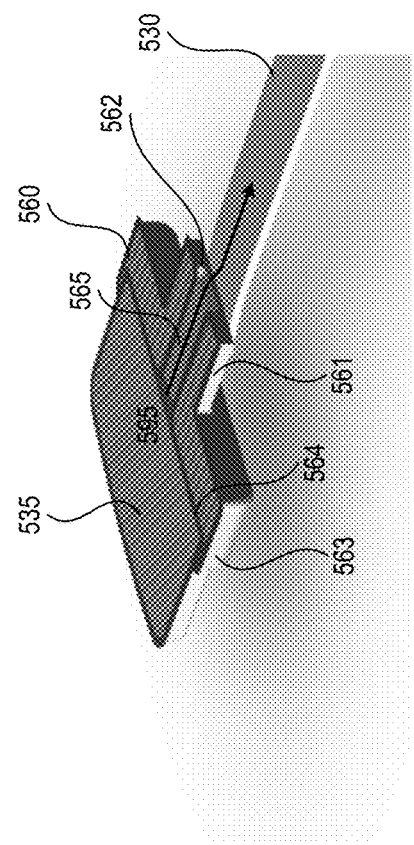
FIG. 5C
FIG. 5D

__HAZARDOUS CONTAMINANT COLLECTION DEVICE WITH INTEGRATED SWAB AND TEST DEVICE__

CROSS REFERENCE TO RELATED APPLICATION

This application is a continuation of U.S. patent application Ser. No. 16/750,343, filed Jan. 23, 2020 and scheduled to issue as U.S. Pat. No. 11,280,801 on Mar. 22, 2022, which claims the benefit of U.S. Provisional Application No. 62/797,804, filed Jan. 28, 2019. Each of the above-referenced applications is hereby incorporated by reference in its entirety.

TECHNICAL FIELD

The systems and methods disclosed herein are directed to environmental contaminant testing, and, more particularly, to a test kit for detecting the presence and/or quantity of antineoplastic agents.

BACKGROUND

Antineoplastic drugs are used to treat cancer, and are most often found in a small molecule (like fluoruracil) or antibody format (like Rituximab). Detection of antineoplastic drugs is critical for determining if there is contamination/leakage in hospital/pharmacy areas where the drugs are used and/or dispensed.

The nature of antineoplastic agents make them harmful to healthy cells and tissues as well as the cancerous cells. Precautions should be taken to eliminate or reduce occupational exposure to antineoplastic agents for healthcare workers. Pharmacists who prepare these drugs and nurses who may prepare and administer them are the two occupational groups who have the highest potential exposure to antineoplastic agents. Additionally, physicians and operating room personnel may also be exposed through the treatment of patients. Hospital staff, such as shipping and receiving personnel, custodial workers, laundry workers and waste handlers, all have the potential to be exposed to these drugs during the course of their work. The increased use of antineoplastic agents in veterinary oncology also puts these workers at risk for exposure to these drugs.

SUMMARY

Existing approaches to detecting a hazardous drug contamination require the user to manually handle sample swabs directly by hand, press the swab material by hand when wiping a test surface, place the sampled swabs into a test tube/vial, and send the sample-impregnated swab to an outside laboratory for testing. Directly handling a swab embedded with hazardous contamination is potentially dangerous for the test user. Further, these existing approaches use a small cotton swabs on a stick which covers very little surface area, requiring significant work and time from the user. Further, the results can come back weeks (sometimes up to nine weeks) after when the test was taken, delaying any decontamination response.

These and other problems are addressed in embodiments of the collection and testing kit described herein that avoids further spread and exposure of contamination during the process of collecting the sample and quickly provides accurate test results at the site and time of testing. The present technology provides a collection device and detection system for testing of various surfaces in healthcare settings for the presence of antineoplastic agents while minimizing user exposure to these agents. The collection device is capable of detecting even trace amounts of antineoplastic agents and of providing results quickly (including immediately after collection). Advantageously, testing and detection occur at the location of the collection. The collection device provides a swab that is simple to use, easy to hold and grip, allows for swabbing of large surfaces, and keeps the user's hands away from the surface and fluid being tested. Beneficially, the swab is integrated with the test assay in a fluid-tight manner, providing for leak-free transfer of the collected fluid from the swab to the assay. As such, the collection device includes the swab, optionally a fluid reservoir, and an assay (or other detection system) integrated into a single, fluid-tight device.

One suitable detection system includes an immunoassay device. Immunoassay devices play an important role in areas such as clinical chemistry and have been made portable for use in the field. Immunoassay technology provides simple and relatively quick means for determining the presence of analytes in a subject sample. Analytes are substances of interest or clinical significance that may be present in biological or non-biological fluids. The analytes can include antibodies, antigens, drugs, or hormones. The analyte of interest is generally detected by reaction with a capture agent, which yields a device more easily detected and measured than the original analyte. Detection methods can include a change in absorbance, a change in color, change in fluorescence, change in luminescence, change in electrical potential at a surface, change in other optical properties, or any other easily measured physical property indicating the presence or absence of an analyte in a sample.

Accordingly, one aspect relates to a hazardous contamination detection system including a collection device. The collection device includes an elongate body forming an enclosure. The collection device also includes an assay test strip disposed within the enclosure. The assay test strip includes a reaction zone configured to produce an optically-detectable change in appearance in the presence of a hazardous contaminant. The collection device also includes an absorbent swab material coupled to the elongate body. The swab material is moistened with a solution configured to lift the hazardous contaminant from a test surface. The elongate body forms a handle having a first end coupled to the absorbent swab material, a second end spaced apart from the first end, and an elongate length extending therebetween. The collection device further includes a fluid-tight enclosure including a fluid pathway between the absorbent swab material and the test strip.

Another aspect relates to a hazardous contaminant collection device. The hazardous contaminant collection device includes an elongate body forming an enclosure. The hazardous contaminant collection device also includes an assay test strip disposed within the enclosure. The assay test strip includes a reaction zone configured to produce an optically-detectable change in appearance in the presence of a hazardous contaminant. The hazardous contaminant collection device also includes an absorbent swab material coupled to the elongate body. The swab material is moistened with a solution configured to lift the hazardous contaminant from a test surface. The elongate body forms a handle having a first end coupled to the absorbent swab material, a second end spaced apart from the first end, and an elongate length extending therebetween. The hazardous contaminant collection device also includes a fluid-tight enclosure including a fluid pathway between the absorbent swab material and the test strip.

Still another aspect relates to a method of testing a test surface for the presence of a hazardous contaminant. The method includes removing a cap from an elongate body of a collection device to expose an absorbent swab material coupled to an end of the elongate body. The absorbent swab material is pre-moistened with a first volume of a solution configured to lift the hazardous contaminant from the test surface. The method also includes wiping the test surface with the absorbent swab material to collect the hazardous contaminant from the test surface. The method further includes reapplying the cap to the elongate body to seal the absorbent swab material to isolate the collected hazardous contaminant within the collection device. The method also includes transferring a volume of liquid from the absorbent swab material to an assay test strip via a fluid-tight path within the collection device, wherein the assay test strip is sealed within the collection device. The method further includes inserting the assay test strip into an assay reader device. The method also includes identifying that the hazardous contaminant is present on the test surface based on an output of the assay reader device.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 4A-4D depict an embodiment of a collection device with an integrated swab material and assay device.

FIGS. 5A-5G depict another embodiment of a collection device with an integrated swab material and test device.

DETAILED DESCRIPTION

Introduction

Figure 1:
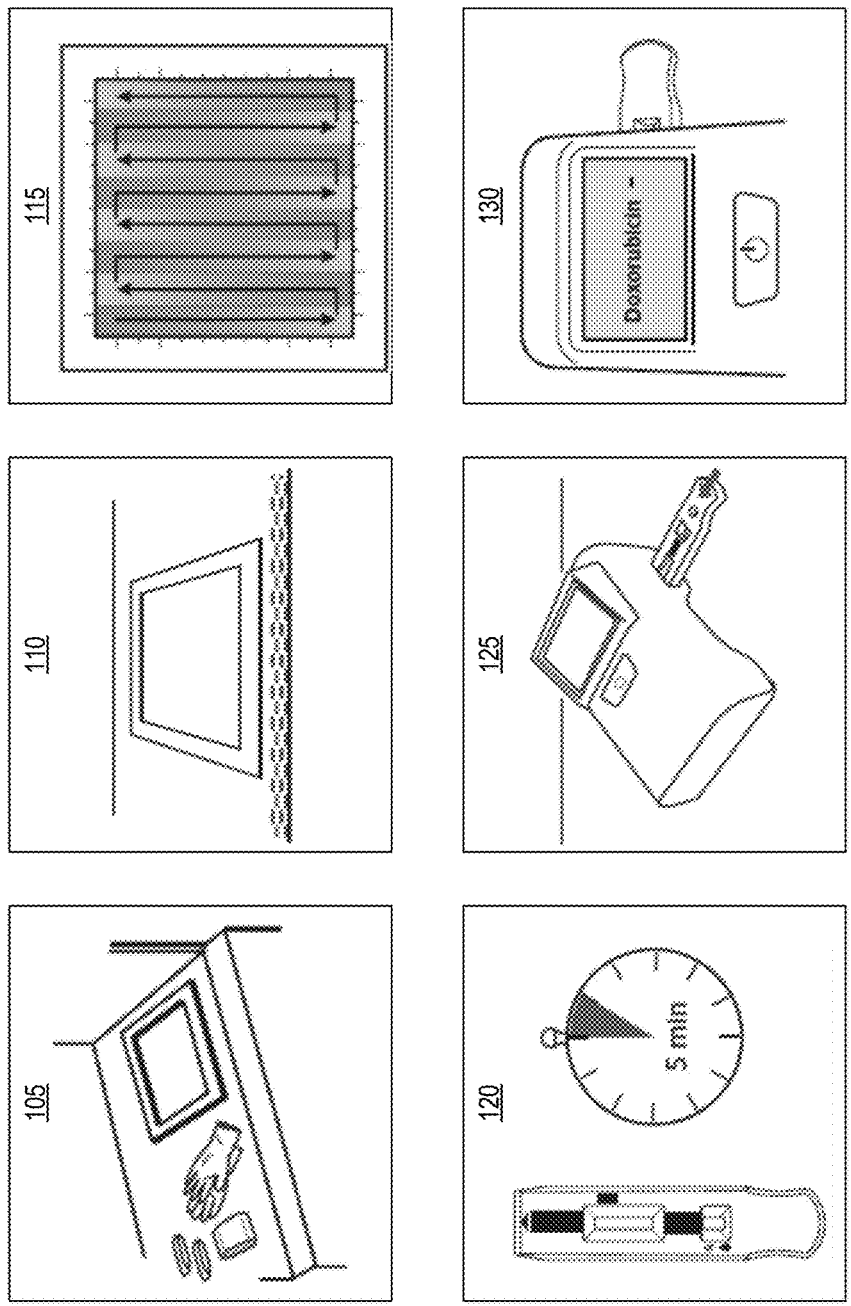
FIG. 1 illustrates example steps of a testing method using a contaminant collection device as described herein.

Embodiments of the disclosure relate to systems and techniques for detection of hazardous environmental contaminants, such as but not limited to antineoplastic drugs used in the treatment of cancer, while minimizing exposure of the test operator to the contaminants. A kit for such testing can include a collection device and a testing device. Throughout this disclosure, example systems, kits, and methods will be described with reference to collection, testing, and detection of antineoplastic agents, but it will be understood that the present technology can be used to collect, test, and detect any particle, molecule, or analyte of interest.

A collection device can include an integrated swab and testing apparatus such as a lateral flow assay test strip. Beneficially, the collection device provides a fluid-tight fluid path between the swab and the test strip, such that the user is protected from collected liquid as it is transferred from the swab to the test strip. The collection device can also include a cap or other container for sealing the swab after collection of the antineoplastic agent. Optionally, a reservoir for containing fluid such as a buffer solution can be disposed in the cap for flushing the swab after sample collection. The swab can be constructed from a special material having desired pickup efficiency and shedding efficiency for detecting trace amounts of antineoplastic agents, and is provided on a handle having sufficient length so that the user can swab a surface without physically contacting the surface or the swab. The handle can perform a double function by serving as the cartridge enclosing the test strip, and interior features of the handle can form the fluid path between the swab and the test strip. A liquid, for example a buffer solution, can be provided on the swab material so that the user removes a pre-wetted swab to swipe the surface in one implementation. In another implementation, the user sprays the surface with a liquid and collects this liquid with the swab material. Tris buffer and ChemoGlo solution are two suitable buffer solutions that can be implemented in contamination collection devices described herein.

The collection kit can further include a template, guide, or instructions to delineate a specific dimensional area for testing. In order to obtain an accurate test result for contaminants that are hazardous even in trace amounts, a precise method of marking (demarcation) and then performing the sampling procedure (for example, to sample all of the demarcated area and only the demarked area) can be a very important step to ensure an accurate result. There are several factors that can be key to obtaining an accurate drug concentration measurement given in the following formula:

$$C = \frac{\alpha * A * \eta_p * \eta_e}{V_b}$$

where C is the concentration, a is the contamination surface density (ng/ft^2), A is the surface area swabbed and tested, $\eta_p$ is the pick-up efficiency, $\eta_e$ is the extraction from the swab density, and $V_b$ is the fluid volume of the buffer solution used to help extract and carry the contamination to the test strip. A goal of the described testing can be to have a high concentration signal with low variability. Excessive "noise" or variation in the variables may cause the test to either give false positive or false negative results. Test kits described herein can include mechanisms and/or instructions to users to assist in reducing the variation of each term in the above concentration equation.

After swabbing the surface, the user places the cap over the swab to form a liquid-tight, sealed compartment that encapsulates the swab material and any absorbed liquid. The cap can additionally lock to the handle. A reservoir in the handle and/or cap can contain a buffer or diluent solution used as an agent to help remove the particles of interest embedded on the swab material into the fluid of the container. The collection device advantageously prevents liquid from spilling and contaminating surfaces or users, but provides for controlled delivery of fluid to a detection device such as a test strip. Fluid can be wicked directly from the swab material to the test strip in some embodiments, and in other embodiments fluid can be released from the swab material along a fluid path to a receiving zone of an assay test strip.

It will be understood that signals generated by embodiments of lateral flow assay devices described herein can be detected using any suitable measurement system, including but not limited to visual inspection of the device and optical detection using an optical reader. In one aspect, the testing device can be an immunoassay reader, for example a lateral flow assay and reader device, with an interface that alerts the user to the presence and/or degrees of contamination. After sample collection with the integrated swab material, the assay test strip can be inserted into a reader to image the indicators on the strip, analyze the image(s), determine a level of contamination, and report the determined level of contamination to the user. The reader can have more than one method of entering data regarding the sample and can have various ways of saving, storing, displaying, uploading and alerting the appropriate personnel when unacceptable levels of contamination are detected.

In one example, after detecting contamination in an initial test there can be several possible next steps. A first option can be to use another more sensitive test strip to determine an advanced level of detection. A second option can be to use another similar test strip in an area near the initial test area to determine the spread of the contamination. A third option can be to initiate any specified decontamination protocol in the area of the test surface (and potentially surrounding areas). It will be understood that some or all of these non-limiting options can initiated simultaneously or sequentially.

The described swabs, buffer solutions, and test devices can be configured to pick up and detect trace amounts of antineoplastic agents and/or chemotherapeutic drugs in some embodiments. It will be appreciated that the described systems can be adapted to collect and detect quantities of other biohazardous chemicals, drugs, pathogens, or substances in other embodiments. Further, the disclosed systems can be used in forensic, industrial, and other settings.

Although the disclosed detection devices are typically described herein with reference to test strips and lateral flow assay reader devices, it will be appreciated that the described hazardous contaminant detection aspects described herein can be implemented in any suitable detection system. For example, features described herein can be implemented in reader devices that analyze other types of assays, such as but not limited to molecular assays, and provide a test result. Further, the fluid including any collected contaminants can be transferred from the collection device to a centrifuge, spectrometer, chemical assay, or other suitable test device to determine the presence and/or concentration of one or more hazardous substances in the sample.

Drugs successfully treat many types of illnesses and injuries, but virtually all drugs have side effects associated with their use. Not all adverse side effects classify as hazardous, however. In the present disclosure, the term "hazardous drugs" is used according to the meaning adopted by the American Society of Health-System Pharmacists (ASHP), which refers to a drug as hazardous if studies in animals or humans have indicated that exposures to them have any one of four characteristics: genotoxicity; carcinogenicity; teratogenicity or fertility impairment; and serious organ damage or other toxic manifestation at low doses in experimental animals or treated patients.

Although described in the example context of ascertaining the concentration of hazardous drugs such as antineoplastic agents, it will be appreciated that the disclosed test strips and reading techniques can be used to detect the presence and/or concentration of any analyte of interest. An analyte can include, for example, drugs (both hazardous and non-hazardous), antibodies, proteins, haptens, nucleic acids and amplicons.

Various embodiments will be described below in conjunction with the drawings for purposes of illustration. It should be appreciated that many other implementations of the disclosed concepts are possible, and various advantages can be achieved with the disclosed implementations.

Overview of Example Contaminant Collection

FIG. 1 illustrates example steps of a testing method 100 using a system contaminant collection device according to the present disclosure, such as but not limited to those shown in FIGS. 2A-2C and 4A-6E. One, some, or all of the depicted blocks of FIG. 1 can be printed as graphical instructions on the packaging or instruction materials of an assay and/or collection kit, or can be presented on a graphical user interface of a display screen of an assay reader device, a test area terminal, or a personal computing device of the user.

At block 105, the user can identify a sample location and gather testing supplies including a collection kit and protective wear. The collection kit can include a collection device including a swab material on an elongate handle, as described herein, for example in a sealed package. In some examples, the swab is pre-wetted with buffer solution and packaged in a sealed pouch. In some implementations, a removable cap can seal the swab material prior to use. The assay cartridge can form some or all of the handle. The assay cartridge may include an assay device housed inside a cartridge having a window or port aligned with a reaction zone of the assay device. In one implementation, the assay device is a test strip, for example but not limited to a lateral flow assay test strip. Also at block 105 the user can put on clean gloves prior to each sample collection and/or opening of the collection kit, both to protect the user from potential contamination on the surface and to protect the collection device from any contamination on the user's hands. The collection kit can also include a template for demarcating the area to be tested on the test surface, though in some examples the template may be provided separately. The collection kit may also include additional buffer fluid for wetting the test surface, though in some examples this can be provided on a pre-moistened swab material.

At block 110, the user can establish a test area on the test surface. For example, the user can place a template over the intended location to clearly demarcate the area that will be swabbed. The template can be a physical template as shown, or may be provided via augmented reality (e.g., smart glasses, a heads up display, a projection onto the test surface). Also at block 110 the user can open the collection kit packaging, including opening the integrated swab and assay cartridge. The test area may be one square foot in some embodiments, for example demarcated as a 12 inches by 12 inches (144 square inches) region. Other examples can use greater or smaller areas for collection including 10 inches by 10 inches, 8 inches by 8 inches, 6 inches by 6 inches and 4 inches by 4 inches, non-square rectangular regions (e.g., a 9 inches by 16 inches rectangle), and non-rectangular regions (e.g. circles). Different-sized templates may be specified for use with different test surfaces. The particular template used can be indicated to a reader device, for example via a manual user input or via a barcode or other identifying pattern on the template scanned by the reader device. For example, a template providing a swab area of a 12 inches by 12 inches region can be indicated for use in sampling a countertop, while a smaller template demarcating a smaller swab area can be indicated for swabbing an IV pole. The reader device can adjust its test result calculations to account for the actual area tested, as indicated by the particular template used for the sampling procedure.

At block 115, the user can swab the entire test area with the pre-moistened swab. The user can swab the test area using slow and firm strokes. As shown, the user can methodically pass the swab in straight lines along the height of the test area all the way across the width of the test area. In embodiments using augmented reality templates, the user can be provided with a visual indication of one or more of the already-swabbed portions of the test region, to-be-swabbed portions of the test region, and swab pattern. As the user swabs the surface, the swab material of the collection device can pick up contaminant particles and/or any buffer liquid provided on the test surface. After swabbing is complete, the user can seal the exposed swab material of the collection device, for example by applying a cap that engages with the assay cartridge and/or handle and seals the swab material. Optionally, the cap can include an additional quantity of buffer solution and a mechanism for releasing this buffer solution onto the swab material to flush collected contaminants downstream to the assay device.

At block 120, the user can use a timer to allow the sample to develop for a period of time. For example, the sample can develop for about one minute, about two minutes, about three minutes, about four minutes, about five minutes, about six minutes, or some other amount of time. Other development times are possible. In some embodiments the timer can be built in to the programming of the reader device that reads the assay. The development time can vary depending on the particular test that is being performed and the particular operating parameters of the assay device. In some embodiments, at least some liquid may be transferred from the swab material to the assay device during swabbing, and the development time can include some or all of the time taken at block 115 to swab the surface. In some embodiments, a valve or frangible seal can isolate the assay device from the collected liquid during swabbing at block 115, and after completion of the swabbing the user can cause the breaking or opening of this seal to transfer the liquid from the swab material to the assay device. In such embodiments, development time may not include any of the swabbing time.

At block 125, the user can insert the assay cartridge into an assay reader device. The assay cartridge can be inserted into the reader device prior to or after the sample is developed, depending upon the operational mode of the device. In some embodiments, the user may sequentially insert multiple cartridges for testing different aspects of the test surface or for ensuring repeatability of test results. Although the cartridge shown in block 125 is not depicted with swab material, it will be appreciated that in some embodiments the integrated swab material may remain affixed to the cartridge as it is inserted (via the end opposite the integrated swab material) into the reader device.

At block 130, the assay reader device reads portions of the inserted cartridge (including, for example, detecting optical signals from exposed areas of a capture zone of a test strip housed in the cartridge), analyzes the signals to determine optical changes to test zone location(s) and optionally control zone location(s), determines a result based on the optical changes, and displays the result to the user. The device can optionally store the result or transmit the result over a network to a centralized data repository. As illustrated, the device displays a negative result for the presence of Doxorubicin in the sample. In other embodiments the device can display a specific detected concentration level in the sample and/or determined for the test area, and optionally can display confidence values in the determined result.

After testing the user can dispose of the collection device and assay (for example in compliance with hazardous waste regulations). Optionally, the user can connect the reader device to its power supply, execute any needed decontamination procedures, re-test a decontaminated surface, and perform required reporting of the result. Though not illustrated in FIG. 1, further steps can include operating the reader device to perform analysis of the test strip. An example of the cartridge inserted into a reader device is shown in FIG. 3A, and an example of the reader device displaying test results is shown in FIG. 3B.

Figure 2A:
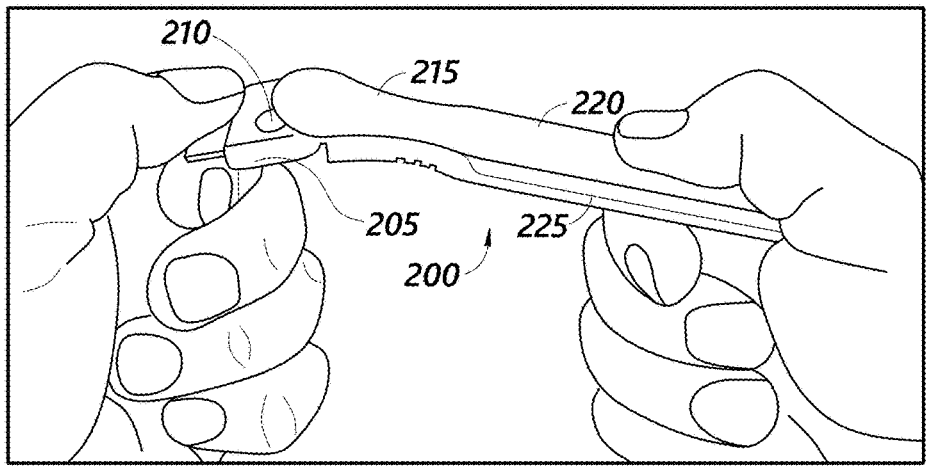
FIGS. 2A-2C show example steps of using a collection device with an integrated swab and test strip during various portions of the testing method of FIG. 1.
Figure 2B:
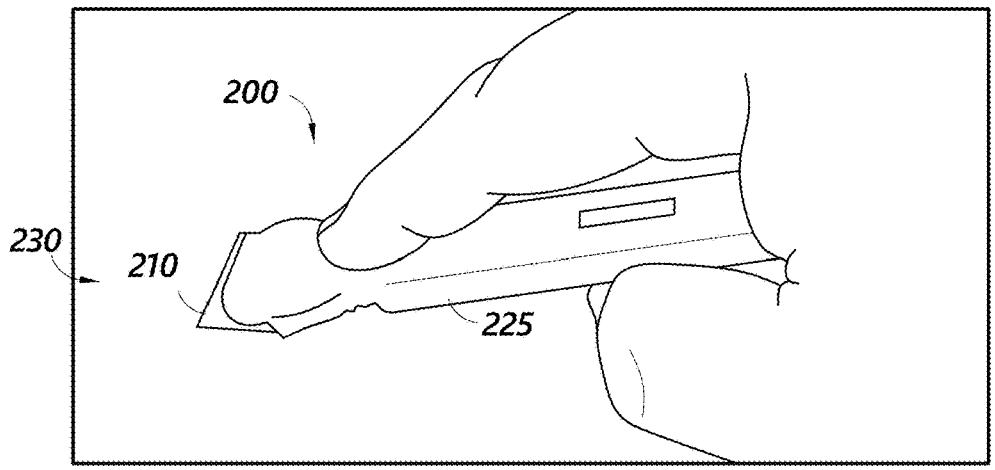
Figure 2C:
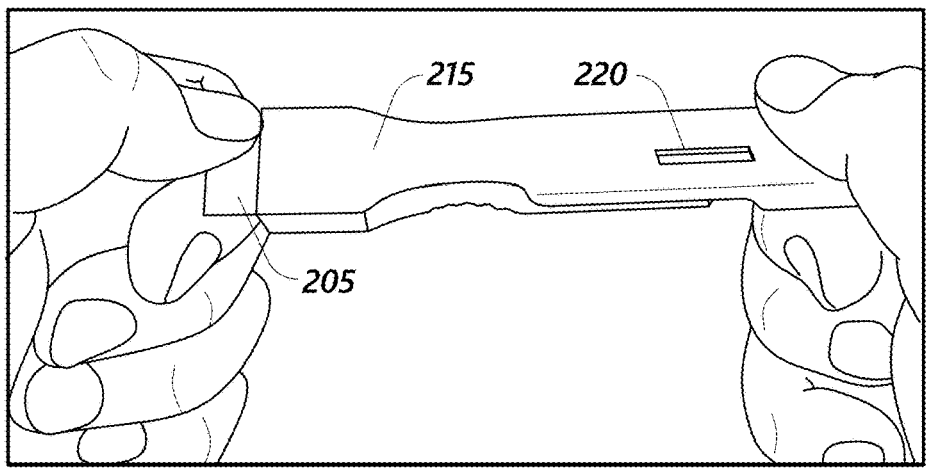

FIGS. 2A-2C show example steps of using a collection device with an integrated swab and test strip during various portions of the process 100. Specifically, FIG. 2A shows a user holding a collection device 200 according to one implementation of the present disclosure. The collection device includes an integrated swab handle/assay cartridge 225. FIG. 2A also shows the user removing a cap 205 from a distal end 215 of the integrated swab handle/assay cartridge 225 to expose a swab material 210. This can happen before block 115 of the testing method 100. FIG. 2A also shows a window 220 in the integrated swab handle/assay cartridge 225 for viewing a reaction zone of a test strip contained within the integrated swab handle/assay cartridge 225. FIG. 2B shows the user holding the integrated swab handle/assay cartridge 225 with the swab material 210 applied to a test surface 230, for example during block 115 of the testing method 100. FIG. 2C shows the user holding the collection device 200 after completion of the swabbing with the cap 205 reapplied, for example after block 115 of the testing method 100. Further details of collection devices with an integrated swab and test strip are described below.

Figure 3A:
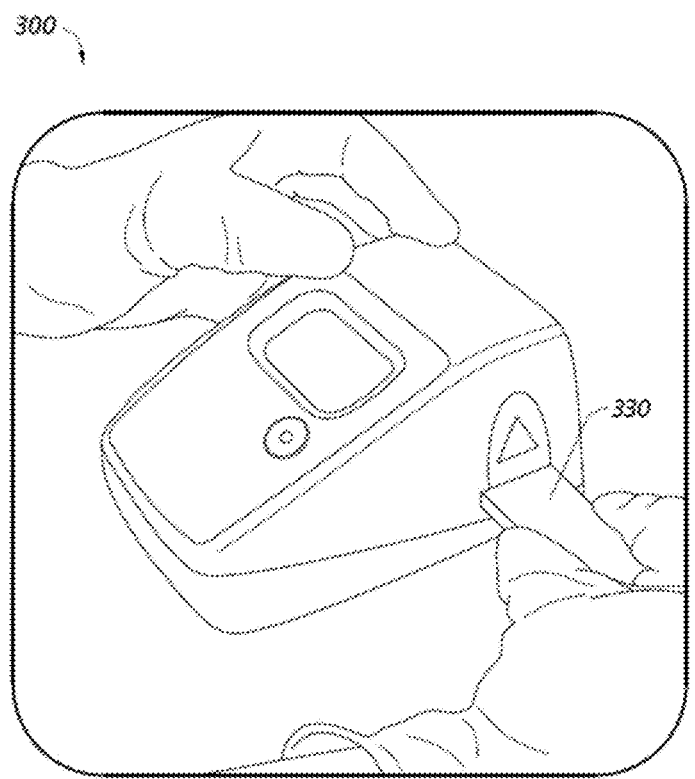
FIGS. 3A and 3B illustrate an example testing device that can be used with the testing method of FIG. 1.
Figure 3B:
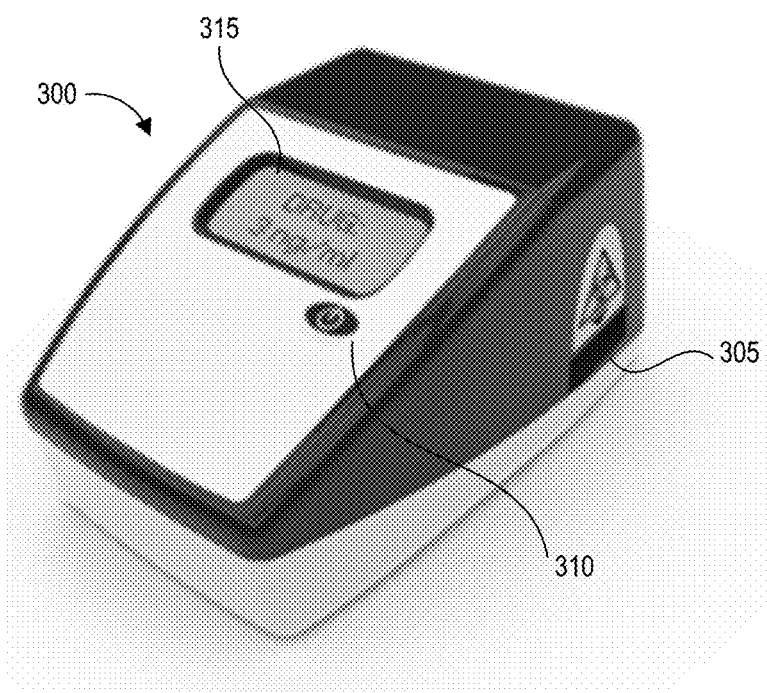

FIGS. 3A and 3B illustrate an example reader device 300 that can be included in or used with hazardous contamination detection kits described herein. FIG. 3A illustrates the reader device 300 with an assay cartridge 330 inserted into a cartridge receiving aperture 305, and FIG. 3B illustrates the reader device 300 without an inserted cartridge. Examples of the assay cartridge 330 include but are not limited to the integrated handle and cartridge shown in FIGS. 2A-2C and 4A-6E.

The reader device 300 can be an assay reader device having an aperture 305 for receiving an assay test strip and cartridge 330. The aperture 305 can also be configured to position the test strip so that analyte binding regions are positioned in an optical path of imaging components located inside of the device 300. The device can also use these or additional imaging components to image a bar code on the cartridge, for example to identify which imaging techniques and analysis to perform.

Some embodiments of the device 300 can be configured to perform an initial scan, for example using a bar code scanner to image one or more bar codes. A bar code can identify the type of test to be performed, the person conducting the test, the location of the test, and/or the location in the facility of the test surface (for example pharmacy, nursing area, cabinet #, bed #, chair #, pump #, etc.). After reading the bar code identifier the cartridge is then inserted into the reader as shown in FIG. 3A. The device 300 can have a button 310 that readies the device for use and provides an input mechanism for a user to operate the device.

The device 300 can also include a display 315 for displaying instructions and/or test results to the user. After insertion of the test strip, the device 300 can read a bar code on the assay test strip to identify the name and/or concentration range of the drug. The device 300 can image the inserted test strip, and analyze the signals representing the imaged test strip to calculate results, display the results to the user, and optionally transmit and/or locally store the results. The results can be calculated and displayed as contamination with an indication of positive or negative (for example, +/−; yes/no; etc.), and/or the actual contamination per area (for example, Drug Concentration=0.1 ng/cm2) and/or per volume (for example, Drug Concentration=3 ng/ml)

Some embodiments of the device 300 may simply display the result(s) to the user. Some embodiments of the device 300 may also store the result(s) in an internal memory that can be recalled, for example, by USB connection, network connection (wired or wireless), cell phone connection, near field communication, Bluetooth connection, and the like. The result(s) can also automatically be logged into the facility records and tracking system. The device 300 can also be programmed to automatically alert any additional personnel as required, without further input or instruction by the user. For example, if the device 300 reads contamination levels that are above the threshold of human uptake and considered hazardous to for human contact, a head pharmacist, nurse, manager, or safety officer can be automatically notified with the results and concentration of contamination to facilitate a rapid response. The notification can include location information, such as but not limited to a geographic position (latitude/longitude) or description of location (Hospital A, Patient Room B, etc.). That response may include a detailed decontamination routine by trained personnel or using a decontamination kit provided together or separately from the hazardous contamination detection kit.

In some embodiments, device 300 can be a special-purpose assay reader device configured with computer-executable instructions for identifying trace concentrations of contaminants in the samples applied to test strips. Further components of the device 300 are discussed below with respect to the diagram of FIG. 7.

Overview of Example Collection Devices with Integrated Swab and Test Strip

As described herein, the contaminant collection devices according to the present disclosure can be "closed systems," referring to the transfer of fluid from the swab material to the assay test strip via a liquid-tight transfer mechanism. For example, the swab material and detection device (such as a test strip) can be fluidically coupled together within a housing to provide a fluid tight seal between the swab material and the test strip (and any intervening fluid path of the collection device). Beneficially, harmful fluids, drugs, or vapors can be completely contained within such a collection device and not vented into the atmosphere or spilled during transfer between the collector and test device, which would possibly cause harm to the user. Fluid-tight can refer to being liquid impermeable, gas or vapor impermeable, or both, depending upon the properties of the contaminant that the collection kit is designed to detect. Beneficially, this can provide protection to a user of the kit from the potential contaminants in the fluid of the collection device.

The various collection devices disclosed herein are described at times using relative position terms. As used herein, the "upper" surface of a collection device refers to the surface through which the reaction zone of the test device is visible. The "lower" surface opposes this upper surface. The "distal" end refers to the end of the collection device from which swabbing material extends or protrudes. The "proximal" end opposes the distal end, and is typically the end that would be positioned closest to the user during swabbing. In some cases, the proximal end includes the leading edge or surface during insertion into a reader device (e.g., the edge or surface that enters the reader device before other edges or surface of the collection device). An "elongate" body of the collection device as described herein refers to the length of the body (extending between the proximal and distal ends) being greater than a width of the body (extending perpendicularly to the length along the upper or lower surface). For example, the length of an elongate body may be two times, three times, four times, or five times greater than the width (or another multiple of the width, where the multiple is greater than one). It will be understood, however, that implementations of the present disclosure are not limited to the specific shapes, sizes, and configurations of the example implementations described with reference to FIGS. 2A-2C and 4A-6E, and the present disclosure can be implemented in devices having other suitable shapes, sizes, and configurations.

A reaction zone of a test device, such as an assay test strip, can be visible through the housing of a collection device as described herein. Such a reaction zone can be configured to produce an optically-detectable change in appearance in the presence of a hazardous contaminant. This change can include one or more optically-detectable lines that develop if the hazardous contaminant is (or is not) present in the applied sample, as described below.

A test strip can also include a sample receiving zone, for example positioned where the fluid path within the collection device is configured to provide a liquid sample from the absorbent swab material. The sample receiving zone can evenly distribute the sample and direct it to a downstream region of the test strip. The sample receiving zone can optionally include compounds (e.g., buffer salts, surfactants, proteins, etc.) that facilitate interaction between the liquid sample and molecules in other zones. The liquid sample can flow, for example, via capillary action downstream along a substrate of the test strip towards the reaction zone. A conjugate release zone can be disposed along this fluid path, for example containing diffusibly bound molecules that are conjugated to colored or fluorescent label particles. The term "diffusibly bound" refers to reversible attachment or adsorption of the labeled conjugate to the conjugate release zone such that the material moves with the lateral flow when contacted with the liquid sample. The conjugate release zone is configured to release the labeled conjugate upon contact with the moving liquid sample. The liquid sample and labeled conjugate can be carried downstream along the lateral flow path from the conjugate release zone to the reaction zone, where one or more detection zones (formed as lines in some examples, also referred to herein as a reaction zone) have non-diffusibly bound capture reagents immobilized within the zone. The term "non-diffusibly bound" refers to attachment of the capture reagents to the material of the detection zone such that the capture reagent is immobilized and therefore does not move with the lateral flow when contacted with the liquid sample. In competitive assay implementations, the labeled conjugate can compete with the target contaminant molecule for binding with the capture reagents, such that a greater intensity of a detection line indicates a smaller quantity of target contaminant. Competitive assay implementations may be suitable for small molecules, such as some antineoplastic agents. In sandwich assay implementations, the labeled conjugate can bind with a first site of target contaminant and a second site of the target contaminant can bind with the capture reagent immobilized in the detection zone, such that a greater intensity of a detection line indicates a greater quantity of the target contaminant.

Figure 4A:
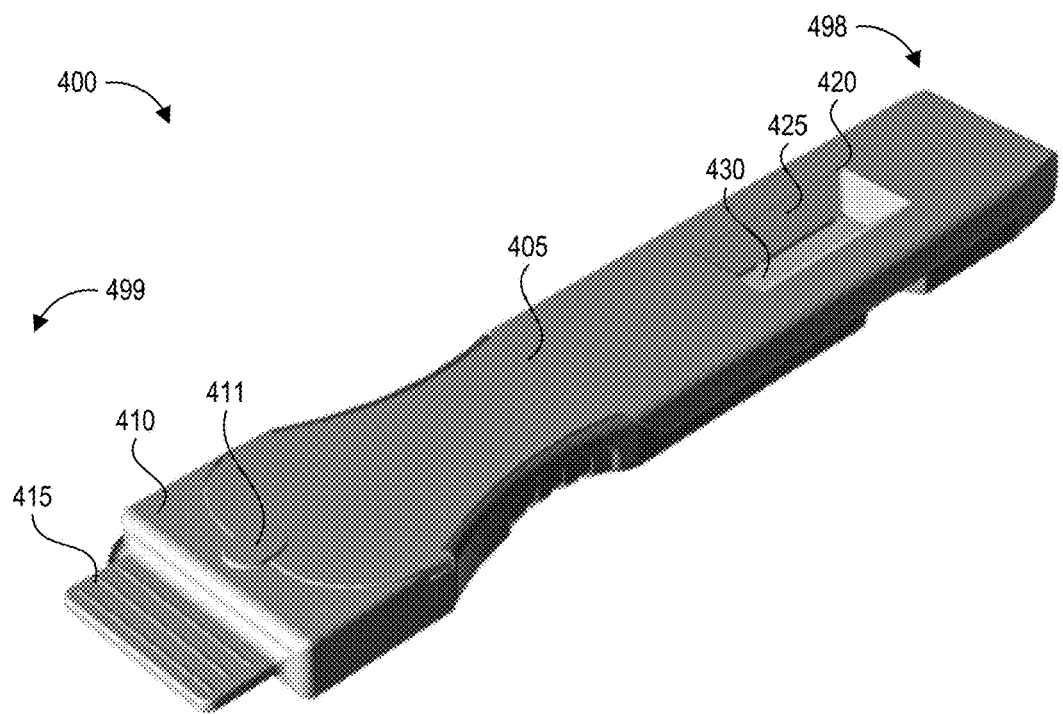
Figure 4B:
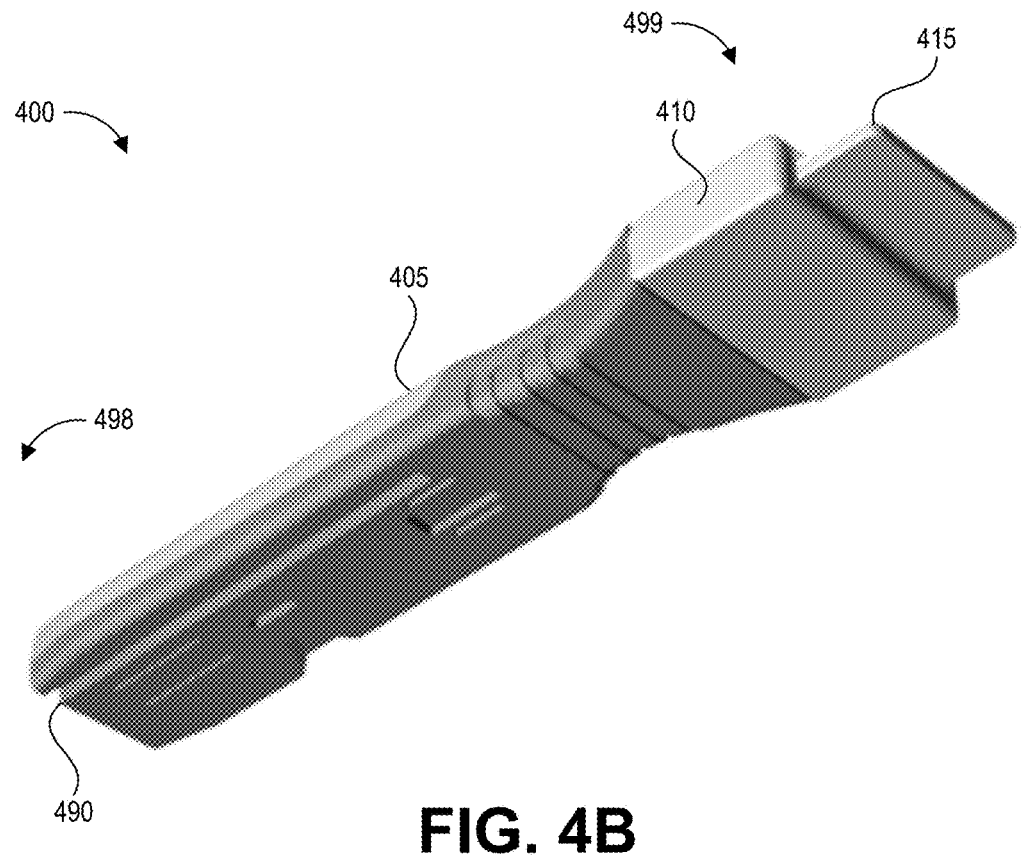

FIGS. 4A-4D depict an embodiment of a collection device 400 with an integrated swab material 435 and test device 430 according to the present disclosure. Specifically, FIG. 4A shows a front (distal end), top (upper surface), and side perspective view of the collection device 400, and FIG. 4B shows a front, bottom (lower surface), and side perspective view of the collection device 400. FIG. 4C shows a top, side perspective view of the collection device 400 without its cap, and FIG. 4D shows the top, side perspective view of the collection device 400 without its upper cartridge portion to reveal the inner components. The model of the collection device 400 depicted in FIGS. 4A-4D can correspond to the collection device 200 depicted in FIGS. 2A-2C. FIGS. 4A-4D are described together below, except where a specific one of FIGS. 4A-4D is noted.

The collection device 400 includes an elongate body 405 that forms an integrated handle and cartridge. The elongate body 405 can be formed from an upper shell and a lower shell coupled together. This elongate body 405 serves to enclose the test strip 430 and fluid path 495 as well as provide an elongate handle for a user to grasp while swabbing a test surface. The elongate body 405 includes an aperture 420 on its upper surface exposing a detection region of the test strip 430. Signals generated at the detection region of the test strip 430 can be detected through a transparent or translucent material forming a window 425 in the aperture 420. The window 425 also maintains a sealed compartment for the test strip 430, which may become saturated with a liquid containing hazardous contaminants. The window 425 may be flat, or may follow the contours of the aperture 420. On its lower surface, the integrated handle and cartridge 405 can include a track recess 490 that can engage a correspondingly shaped protrusion or rail of a reader device when the elongate body 405 is inserted into the reader device. The track recess 490 can be formed in the lower surface and the proximal end 498 of the collection device 400. In other embodiments the track recess 490 can be replaced with a rail or track, with the reader device having a corresponding track recess. Other suitable alignment features can be used in other embodiments. The lower surface can include additional mechanical features (e.g., grooves, detents, protrusions) that mate with corresponding features of the reader device.

FIGS. 4A and 4B show a cap 410 secured to the distal end 499 of the elongate body 405. The cap 405 includes a grip tab 415 to facilitate its removal by a user. The cap 405 also includes a reattachment clip 411. When the user snaps off the cap for sample collection, the cap can be reattached after use by this small clip. The cap 410 covers the swab material 435, which is visible in FIGS. 4C and 4D and extends beyond the distal end 499 of the elongate body 405. Some embodiments can include a semi-rigid sheet of material within or along a surface the swab material 435, which can assist in sample collection by acting as a squeegee and/or backer that supports the swab material 435. For example, a ledge 440 of the upper surface of the elongate body 405 can counter pressure placed on the swab material 435 by a test surface during swabbing and keep the swab material 435 firmly engaged with the test surface. In some embodiments, the cap 410 can be broken away from the elongate body 405, folded at a hinge region to be flush with the bottom of the elongate body 405, and secured there with mechanical mating features. The cap 410 can then be folded back to its original position to re-seal the swab material 435 after swabbing a test surface.

The user can moisten the test surface using a solution, hold the elongate body 405, and pass the swab material 435 along the test surface, for example as described with respect to FIG. 1. The solution can be provided separate from the collection device 400. In this implementation, the user may not have to perform steps of extracting the collected sample from the swab material 435 and homogenizing the sample. Instead, the test strip 430 has been extended along a longitudinal axis of the device in a direction away from the reaction zone and leading to a portion that is widened into the swab material 435, allowing the test strip 430 to function as a collection device in addition to functioning as a detection device. As such, fluid picked up by the swab material 435 is drawn directly into the test strip 430 (which can be a lateral flow assay test strip), for example via capillary action along the fluid path 495. In the embodiment of FIGS. 4A-4D, the fluid path 495 is formed by the continuous material extending from the swab material 435 region to the test strip 430 region. Absorbed fluid can begin to saturate the test strip 430 as enough fluid is absorbed by the swab material 435. As such, processing (e.g., binding of any collected contaminants to compounds in or on the test strip 430) can begin to take place even during swabbing of the test surface and development (e.g., the appearance of one or more optically-detectable signals (such as lines) at the reaction zone) can occur (including one or more optically-detectable signals at a test region if the contents of the absorbed liquid include an analyte of interest and/or one or more optically-detectable signals at a control region confirming that the test strip 430 functions as intended). Signals generated on the test strip 430 can continue to develop until required processing time for result verification is complete.

In some embodiments the test strip 430 and swab material 435 can be a unitary piece of the same material. In other embodiments the swab material 435 can be a different piece of material, potentially a different type of material, affixed to the test strip 430. For example, the swab material 435 can be any suitable material having desired pickup and/or shedding efficiency for a target contaminant, including but not limited to materials described herein. The test strip 430 may be any suitable material, including but not limited to materials having structures (e.g., fibers and/or channels) to wick fluid via capillary action in the direction depicted for the fluid path 495.

Figure 5A:
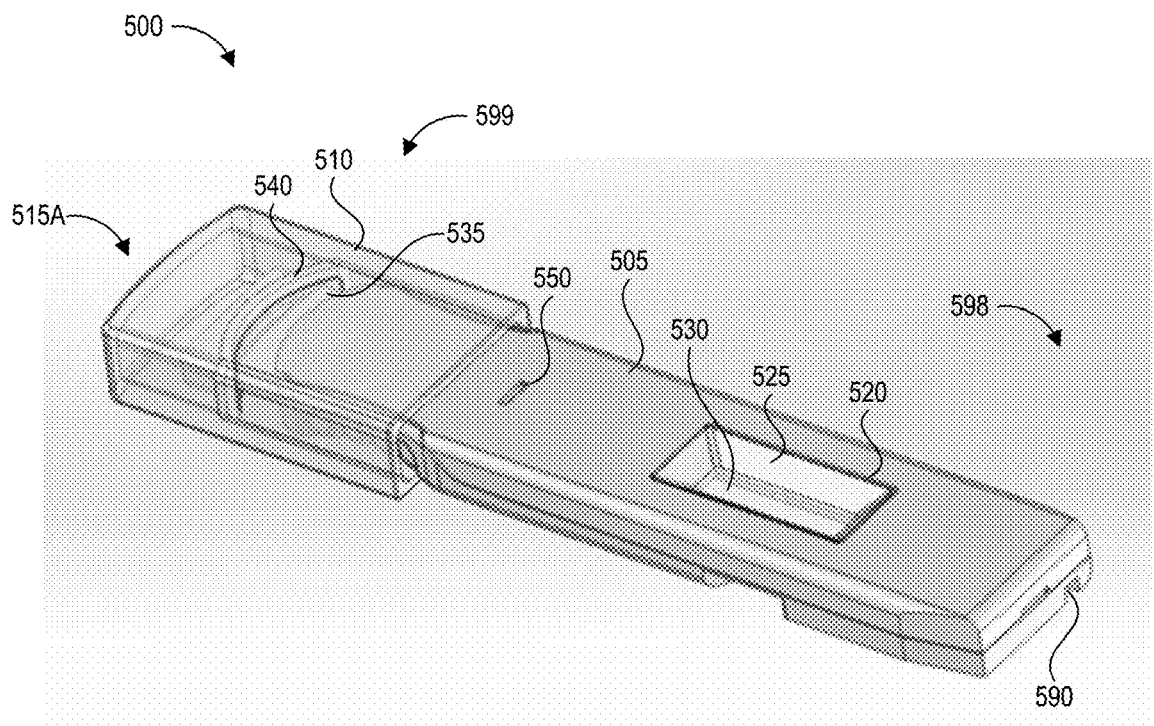
Figure 5B:
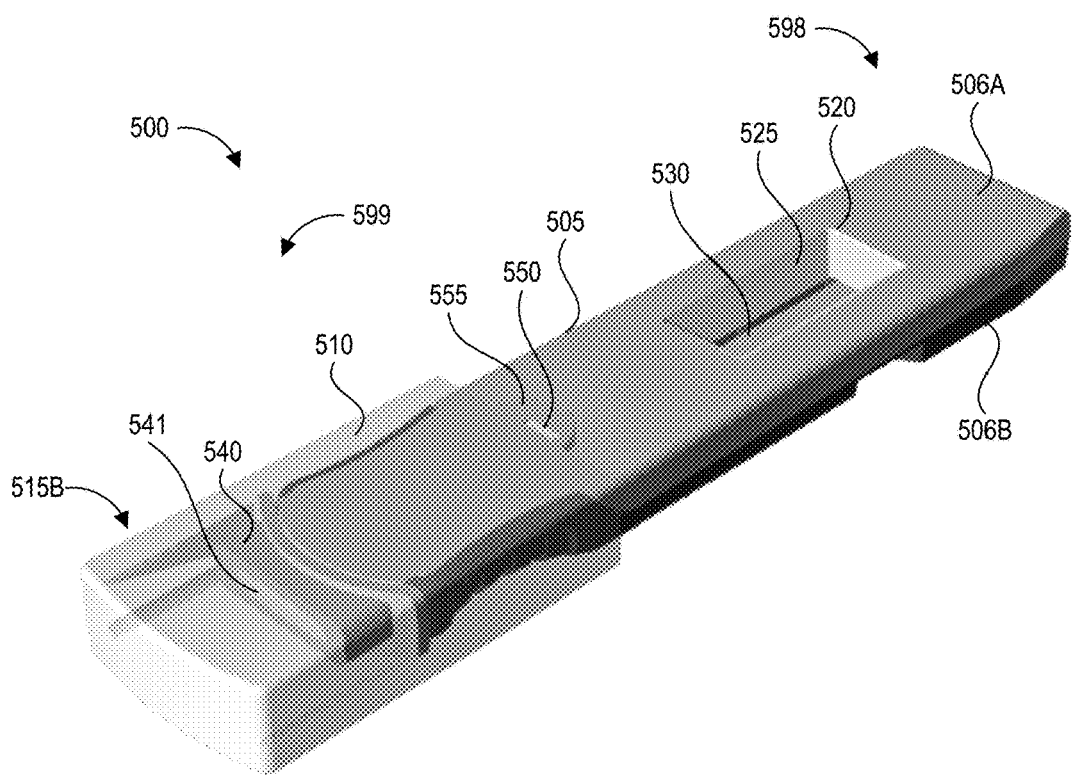

FIGS. 5A-5G depict another embodiment of a collection device 500 with an integrated swab material 535 and a test device 530 according to the present disclosure. Specifically, FIG. 5A shows a back (proximal end), top (upper surface), and side perspective view of the collection device 500 with a cap 510 in a first orientation 515A, and FIG. 5B shows a front (distal end), top, and side perspective view of the collection device 500 with the cap 510 in a second orientation 515B. FIGS. 5A and 5B are described together below, except where a specific one of FIGS. 5A and 5B is noted.

The collection device 500 includes an elongate body 505 that forms an integrated handle and cartridge. The elongate body 505 can be formed from an upper shell 506A and a lower shell 506B coupled together. This elongate body 505 serves to enclose the test strip 530 and fluid path 595 as well as provide an elongate handle for a user to grasp while swabbing a test surface. The elongate body 505 includes an aperture 520 on its upper surface exposing a detection region of the test strip 530. Signals generated at the detection region of the test strip 530 can be detected through a transparent or translucent material forming a window 525 in the aperture 520. The window 525 also maintains a sealed compartment for the test strip 530, which may become saturated with a liquid containing hazardous contaminants. The window 525 may be flat, or may follow the contours of the aperture 520. On its lower surface, the integrated handle and cartridge 505 can include a track recess 590 that can engage a correspondingly shaped protrusion or rail of a reader device when the elongate body 505 is inserted into the reader device. The track recess 590 can be formed in the lower surface and the proximal end 598 of the collection device 500. In other embodiments the track recess 590 can be replaced with a rail or track, with the reader device having a corresponding track recess. Other suitable alignment features can be used in other embodiments. The lower surface can include additional mechanical features (e.g., grooves, detents, protrusions) that mate with corresponding features of the reader device.

FIGS. 5A and 5B show a cap 510 secured to the distal end 599 of the elongate body 505. The cap 510 covers the swab material 535 when applied and extends beyond the distal end 599 of the elongate body 505. The cap 510 includes a swab receiving member 540. In FIG. 5A, the cap 510 is in a first orientation 515A, while in FIG. 5B, the cap 510 is in a second orientation 515B in which it has been flipped over (e.g., rotated 180 degrees around its longitudinal axis) compared to the first orientation 515A. As will be described in further detail below, this change in orientation provides certain benefits. In the first orientation 515A, the swab material 535 (visible in FIG. 5A through the cap 510) abuts a surface of the swab receiving member 540, thereby preventing the distal end 599 of the elongate body 505 from extending fully into the cap 510. This protects the swab material 535 from contamination during shipment and storage. The user may receive the device with the cap in the first orientation 515A, remove the cap 510, perform swabbing as described herein, and then reapply the cap in the second orientation 515B in which the cap is rotated 180 degrees from the position it was in when it was first attached to the device. In the second orientation 515B, the swab material 535 (not visible in FIG. 5B) is fully received by the swab receiving member 540, and the distal end 599 of the elongate body 505 extends fully (e.g., to its maximum possible distance) into the cap 510. This flushes the swab material 535 with a solution stored in the cap as the swab material breaks the seal containing the solution. It will be understood that the cap 510 may not include a swab receiving member 540 in some cases, or may include a swab receiving member 540 that is shaped and sized differently than in this example implementation. In some implementations, the cap 510 includes a tab 555 that engages a detent 550 on the upper surface of the elongate body 505. Further details of the structure of the cap 510 and its orientations are described with respect to FIGS. 5E-5F.

FIG. 5C shows a top view of the collection device 500 without its upper cartridge portion 506A (with only the lower cartridge portion 506B) to reveal the inner components. FIG. 5C also depicts the collection device 500 without the cap 510, illustrating how the swab material 535 extends from the distal end 599 of the elongate body 505 in a direction away from a reaction zone of the test strip 530, and depicting how the swab material 535 can have a tapered distal end 536. Some embodiments can include a semi-rigid sheet of material within or along a surface the swab material 535, which can assist in sample collection by acting as a squeegee and/or backer that supports the swab material 535. FIG. 5D shows the swab material 535, a retaining member 560 configured to retain the swab material 535, and the test strip 530. FIGS. 5C and 5D are described together below, except where a specific one of FIGS. 5C and 5D is noted.

As shown in FIG. 5C, the test strip 530 is housed in an enclosure 570 of the elongate body 505. The enclosure 570 can be considered as the interior cavity of the elongate body 505, formed by interior surfaces of the upper cartridge portion 506A, lower cartridge portion 506B, and retaining member 560. The enclosure 570 can be substantially sealed, for example in a fluid-tight manner, within the elongate body 505. "Substantially sealed" refers to how the enclosure 570 is designed to prevent egress of potentially contaminated fluid from its interior, but still includes the fluid path 595 that allows passage of fluid from the swab material 535 into the enclosure 570 to contact the test strip 530. For example, the enclosure 570 can have a fluid-tight seal along a seam or junction between the upper cartridge portion 506A and lower cartridge portion 506B, and can have a fluid-tight seal along a seam or junction at a distal aperture of the elongate body 505 between the upper cartridge portion 506A, the lower cartridge portion 506B, and the retaining member 560. The channel 565 can enable fluid in the swab material 535 to flow to the test strip 530. The cap 510 (not pictured in FIGS. 5C and 5D) can complete the seal around the enclosure 570 by preventing egress of liquid from the swab material 535 into the environment of the collection device 500.

The retaining member 560 couples the swab material to the elongate body 505 and also provides a fluid path 595 between the swab material 535 and the test strip 530. Specifically, the retaining member 560 includes a distal collar 563 forming a recess 564 that holds a proximal portion of the swab material 535. The retaining member can include a fluid transfer member 561 that extends away from the distal collar 563 and forms a channel 565 leading from the recess 564 to an aperture 562 disposed adjacent to the test strip 530. It will be understood that the retaining member 560 is not limited to the specific configuration described with respect to this example, and can be implemented using different structures that provide a fluid path 595 between the swab material 535 and the test strip 530. As described in more detail below with respect to FIG. 5G, when the cap 510 is pressed onto the elongate body 505 in the second orientation 515B, this can cause compression of the swab material 535 (and can release additional fluid into the swab material 535), pushing fluid through the channel 565 in the direction depicted for the fluid path 595. The distal collar 563 can include a contoured surface 566 that engages with (and in some examples forms a seal with) internal features of the cap 510. Thus, the retaining member 560 secures the swab material 535, provides a fluid path 595 along which fluid can travel from the swab material 535 to the test strip 530, and also forms a seal to enclose the fluid path 595 leading into the enclosure 570.

The user may receive the collection device 500 packaged with the cap 510 applied in the first orientation 515A. As shown in FIG. 5A, in this first orientation 515A, the cap 510 may not engage the detent 550 on the upper surface of the elongate body 505. The swab material 535 can be pre-moistened, for example with a liquid designed to optimize pickup efficiency of the target contaminant from a test surface. In the first orientation 515A, the cap 510 can form a seal with the upper and lower cartridges 506A, 506B to maintain the swab material 535 in its pre-moistened condition. The user can remove the cap 510 and pass the moistened swab material along the test surface, for example as described above with respect to FIG. 1. After the collection procedure is complete, the user can put the cap 510 back onto the elongate body 505 in the second orientation 515B. In this second orientation 515B, as described in further detail below, additional fluid stored within the cap is released onto the swab material 535, causing it to over-saturate and release fluid along the fluid path 595 through the channel 565 to the test strip 530.

Figure 5E:
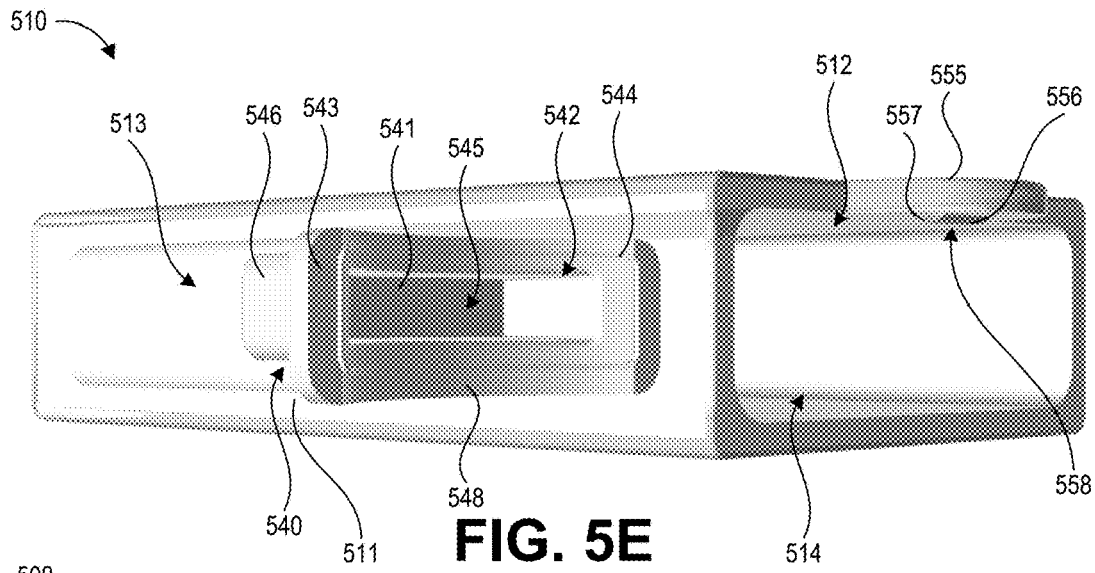
Figure 5F:
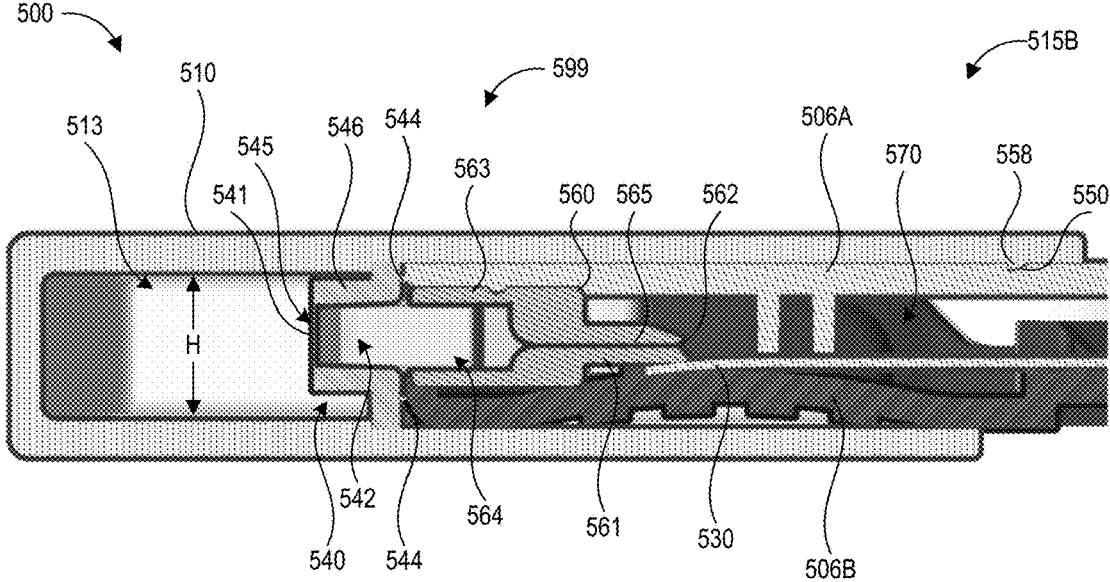

FIGS. 5E-5F illustrate how the cap 510 is configured to both compress the swab material 535 and also flush additional solution through the swab material 535 after the swab material 535 has been used to collect a sample. FIG. 5E shows a perspective view of the cap 510 and the swab receiving member 540 positioned within the interior of the cap 510. The swab receiving member 540 has a lip 543 that engages with an interior wall of the cap 510. The lip 543 can include a contoured surface 548 shaped to match the shape of contoured surface 566 of the swab retaining member 560. A gasket 544 is disposed along the contoured surface 566 to seal with the contoured surface 566. In the depicted example, the gasket 544 and contoured surface 548 are arch-shaped, however the particular design can vary in other implementations.

A wall 546, formed in this example as a rectangular tube, extends away from the lip 543 to form a slot 542 sized and positioned to receive the swab material 535 when the cap 510 is applied to the elongate body 505 in the section orientation 515B. The wall 546 may assume other geometric configurations in other designs such that the shape of the slot 542 generally corresponds to the exterior shape of the swab material 535. In some implementations, the slot 542 may taper along its length to encourage liquid to move backwards through the swab material 535 (e.g., in a direction from the distal end 599 of the collection device 500 toward the proximal end 598 of the collection device 500) as the swab material 535 is inserted into the slot 542.

An aperture 545 is formed at a distal end of the slot 542. In FIG. 5E, the aperture 545 is covered by a frangible seal 541. The frangible seal 541 can be formed from a liquid-tight material that may be pierced, broken, or detached from the wall 546 upon application of a certain amount of force from the swab material 535 (as described with more detail with respect to FIG. 5G). When the seal 541 is opened, fluid can flow from the reservoir 513 into the slot 542 (and any swab material 535 positioned in the slot 542).

The swab receiving member 540 may be a separately manufactured component from the body of the cap 510, and can be inserted into the cap 510 through its proximal aperture 514. The cap 510 can have a ledge 511 that retains the swab receiving member 540 in its proper position within the cap 510 (e.g., positioned so that the swab material 535 will be received in the slot 542). For example, the reservoir 513 of the cap 510 can be filled with liquid, for example a buffer solution designed to flush collected contaminant off of the swab material 535, and then the swab receiving member 540 with the frangible seal 541 sealing the aperture 545 can be inserted into the cap 510. This can seal the liquid in the reservoir 513 of the cap until the frangible seal 541 is broken. Once in place, the swab receiving member 540 can be affixed in place with suitable means including but not limited to pressure, adhesive, ultrasonic welding, and mechanical fasteners.

FIG. 5E also depicts the structure of the tab 555 in greater detail. The tab 555 includes a protrusion 558 on its surface that faces the upper cartridge portion 506A. The protrusion 558 has a sloped or curved surface 556 that faces proximally as the cap 510 is inserted onto the elongate body 505 and a flat surface 557 that faces distally as the cap 510 is inserted onto the elongate body 505. This shape can correspond to the shape of the detent 550 on the elongate body 505 in order to snap the cap 510 into place and/or lock the cap 510 to the elongate body 505 when in the second orientation 515B. It will be understood that other configurations of the tab 555 can be suitably implemented in embodiments of the present disclosure.

FIG. 5F shows a cross-sectional view of the distal end 599 of the collection device 500 with the swab material 535 omitted for ease of viewing other components. In this view, the cap 510 is fully applied to the elongate body 505 in the second orientation 515B. This cross-sectional view illustrates how the recess 564 of the retaining member 560 tapers (e.g., has an increasingly smaller cross section) towards the aperture 545. This cross-sectional view also illustrates how the recess 564 of the retaining member 560 aligns with the slot 542 of the swab receiving member 540 when the cap 510 is applied to the elongate body 505 in the second orientation 515B. The reservoir 513 has a height H along a dimension between the upper surface and the lower surface of the elongate handle 505. This height H can correspond to the height of the elongate handle 505 along the same dimension. As illustrated in FIG. 5F, the slot 542 and recess 564 are vertically offset (e.g., not centered) along the height H. This results in a mismatch between the swab material extending from the recess 564 and the slot 542 when the cap is in the first orientation 515A, such that the swab material 535 abuts the lip 543 rather than entering the slot 542. This can prevent the swab material 535 from breaking the frangible seal 541 when the cap is applied in the first orientation 515A. The vertical offset of the recess 564 can be the same as the vertical offset of the slot 542 along the height H so that they align with one another when the cap 510 is applied to the elongate body 505 in the second orientation 515B.

In this example, the cap 510 has a rectangular cross section, and the second orientation 515B represents reapplication of the cap after a 180 degree rotation (about the cap's longitudinal axis around its length dimension) of the cap 510 relative to the first orientation 515A. Other implementations can structure the cap 510 and the distal end 599 of the elongate body 505 so that other rotations from the first orientation 515A yield the second orientation 515B. For example, in another implementation the cap 510 may have a square, circular, or other rotationally symmetric cross section, and can be rotated any number of degrees less than 360 degrees to switch to the second orientation 515B from the first orientation 515A. FIG. 5F also illustrates how the gasket 544 can seal the negative space formed by the joining of the slot 542 and the recess 564. Beneficially, this can isolate any contaminants collected by the swab material 535 within the sealed enclosure 570, protecting the environment and/or user of the collection device 500 from exposure to potentially hazardous compounds.

Figure 5G:
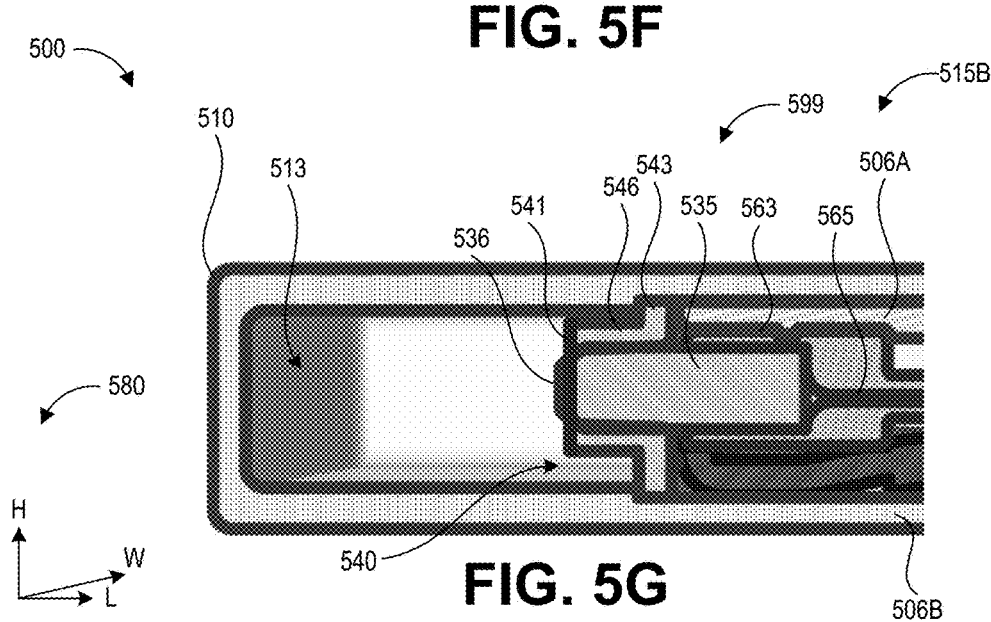

FIG. 5G shows a cross-sectional view of the distal end 599 of the collection device 500 with the swab material 535, and the cap 510 fully applied to the elongate body 505 in the second orientation 515B. FIG. 5G also includes a legend 580 depicting dimensions corresponding to the height (H), length (L), and width (W) of the collection device 500 as shown in FIGS. 5F-5G. This cross-sectional view illustrates the positioning of the swab material 535 relative to the receiving member 540. FIG. 5G depicts the swab material 535 in its original, uncompressed shape, and as such it appears to spatially overlap with the receiving member 540 due to the taper of the slot 542. It will be appreciated that in use the swab material 535 would be compressed to correspond to the taper of the slot 542. In addition, the length of the swab material 535 is greater than the combined length of the slot 542 and the recess 564, such that the tapered distal end 536 extends distally beyond the position of the frangible seal 541. This can cause the frangible seal 541 to break or otherwise open, releasing the fluid of the reservoir 513 into the swab material 535. The tapered distal end 536 can also facilitate insertion of the swab material 535 into the tapered slot 542. As such, the application of the cap 510 in the second orientation 515B, as shown in FIG. 5G, beneficially provides both flushing of the swab material 535 (by breaking the seal 541) and compression of the swab material 535 to encourage flow of fluid (and any collected contaminants) through the channel 565 and onto the test strip 530.

As described above, the test strip 530 can be a lateral flow assay test strip, which may have a predetermined development time for viewing of results of the test. In some embodiments, this development time can begin upon application of the cap 510 in the second orientation 515B, which causes liquid to flush the swab material 535 and carry any collected sample to the test strip 530. After the development time, a user and/or reader device can view the detection region of the test strip 530 to determine the presence and/or concentration of the target contaminant at the test surface, for example based on the number and/or intensity of lines that develop in the detection region.

Figure 6A:
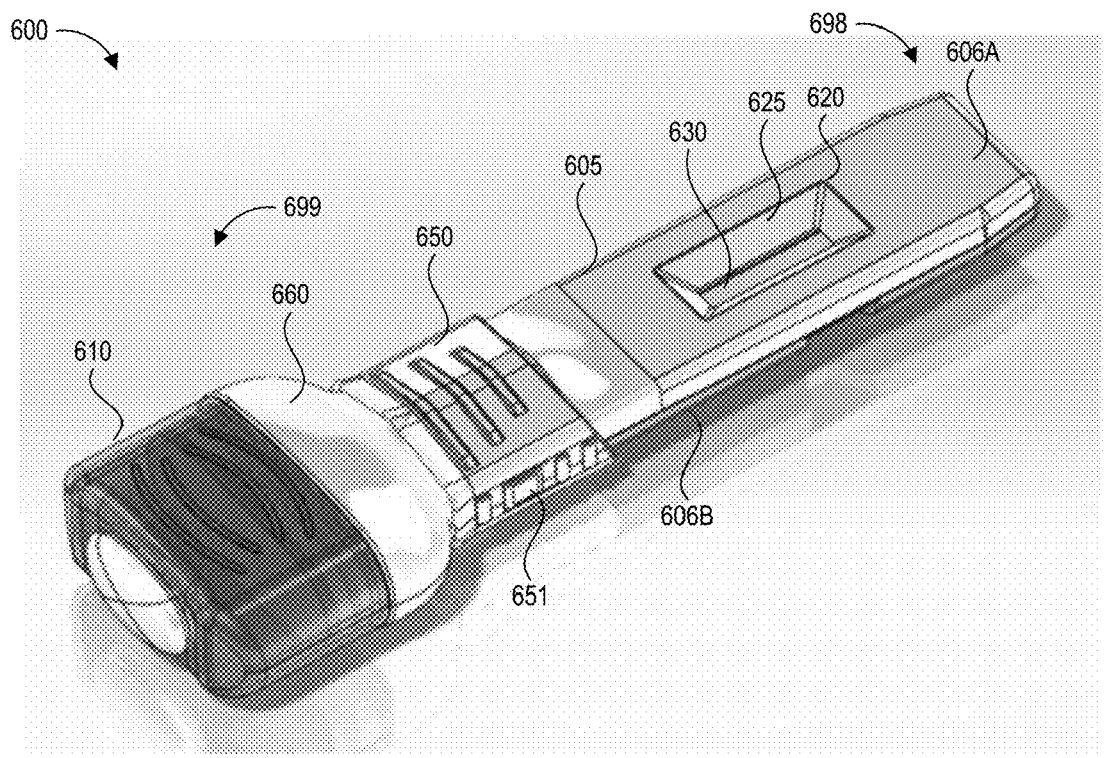
FIGS. 6A-6E depict another embodiment of a collection device with an integrated swab material and test device.
Figure 6B:
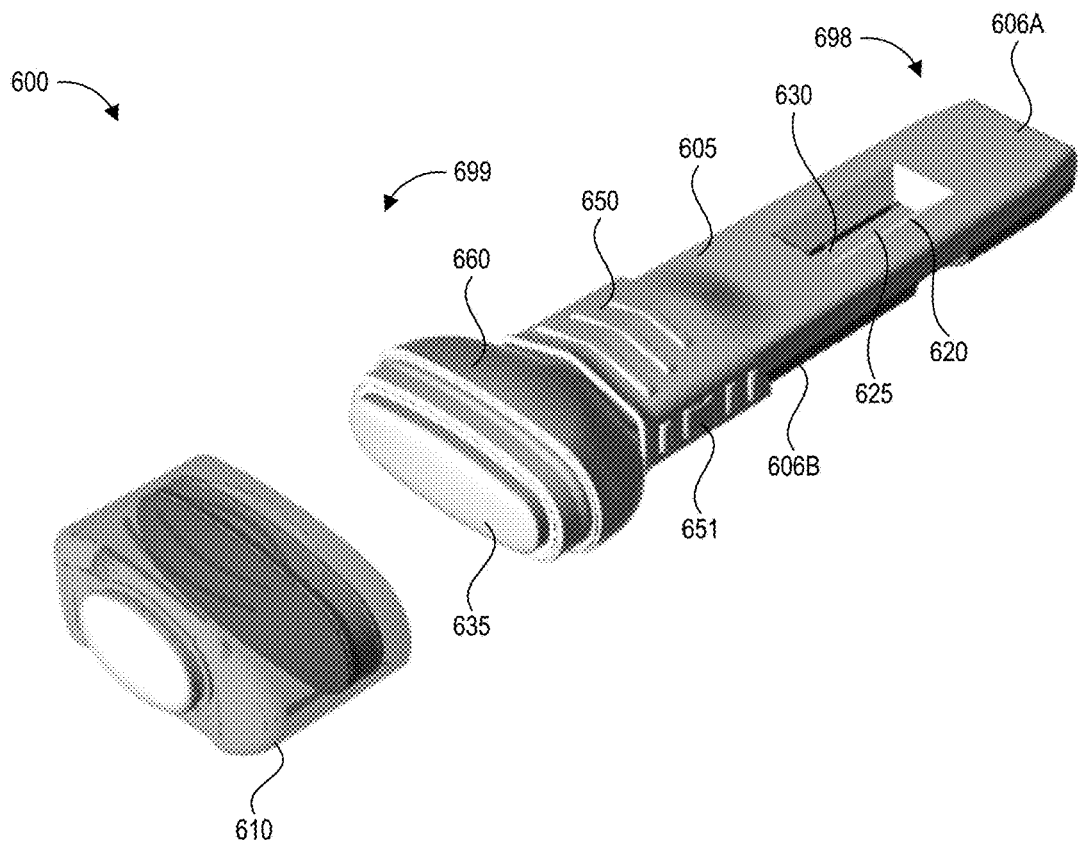

FIGS. 6A-6E depict another embodiment of a collection device 600 with an integrated swab material 635 and test device 630 according to the present disclosure. Specifically, FIG. 6A shows a front (distal end), top (upper surface), and side perspective view of the collection device 600 with a cap 610 applied, and FIG. 6B shows the front, top, and side perspective view of the collection device 600 with the cap 610 removed to expose the swab material 635. FIGS. 6A and 6B are described together below, except where a specific one of FIGS. 6A and 6B is noted.

The collection device 600 includes an elongate body 605 that forms an integrated handle and cartridge. The elongate body 605 can be formed from an upper shell 606A and a lower shell 606B coupled together. This elongate body 605 serves to enclose the test strip 630 and fluid path as well as provide an elongate handle for a user to grasp while swabbing a test surface. The elongate body 605 includes an aperture 620 on its upper surface exposing a detection region of the test strip 630. Signals generated at the detection region of the test strip 630 can be detected through a transparent or translucent material forming a window 625 in the aperture 620. The window 525 also maintains a sealed compartment for the test strip 630, which may become saturated with a liquid containing hazardous contaminants. The window 625 may be flat, or may follow the contours of the aperture 620. On its lower surface, the integrated handle and cartridge 605 can include a mechanical feature (not shown) that can engage a correspondingly shaped mechanical feature of a reader device when the elongate body 605 is inserted into the reader device.

The swab material 635 is secured by a retaining member 660. A collar 650 secures the retaining member 660 to the elongate body 605. As described with respect to FIGS. 6D and 6E, the collar 650 can be slidably engaged with the elongate body 605 such that a user can move the collar 650 (and the attached retaining member 660 and optionally the cap 610) toward the proximal end 698 of the collection device. In some embodiments, a user can press a button 651 to release the collar 650, retaining member 660, and swab material 635 (optionally with the cap 610 attached) from the elongate body 605. The user can separate the collection device 600 into a collection portion (including the collar 650, retaining member 660, swab material 635, and optionally the cap 610) and a test portion (including the elongate body 605 and the test strip 630). Beneficially, this can allow the user to connect the collar 650 to a different elongate body 605A containing another test strip 630A (not illustrated), for example to apply the same collected sample to multiple test strips. As described in more detail with respect to FIGS. 6D and 6E, one or both of the collection portion and the test portion can have sealing features such that their interior enclosures are sealed during the decoupling of the collection portion from the test portion. Beneficially, this can prevent potentially hazardous contamination from spilling during the decoupling and as the separated portions are handled, and can maintain any additional collected sample within the collection portion.

Figure 6C:
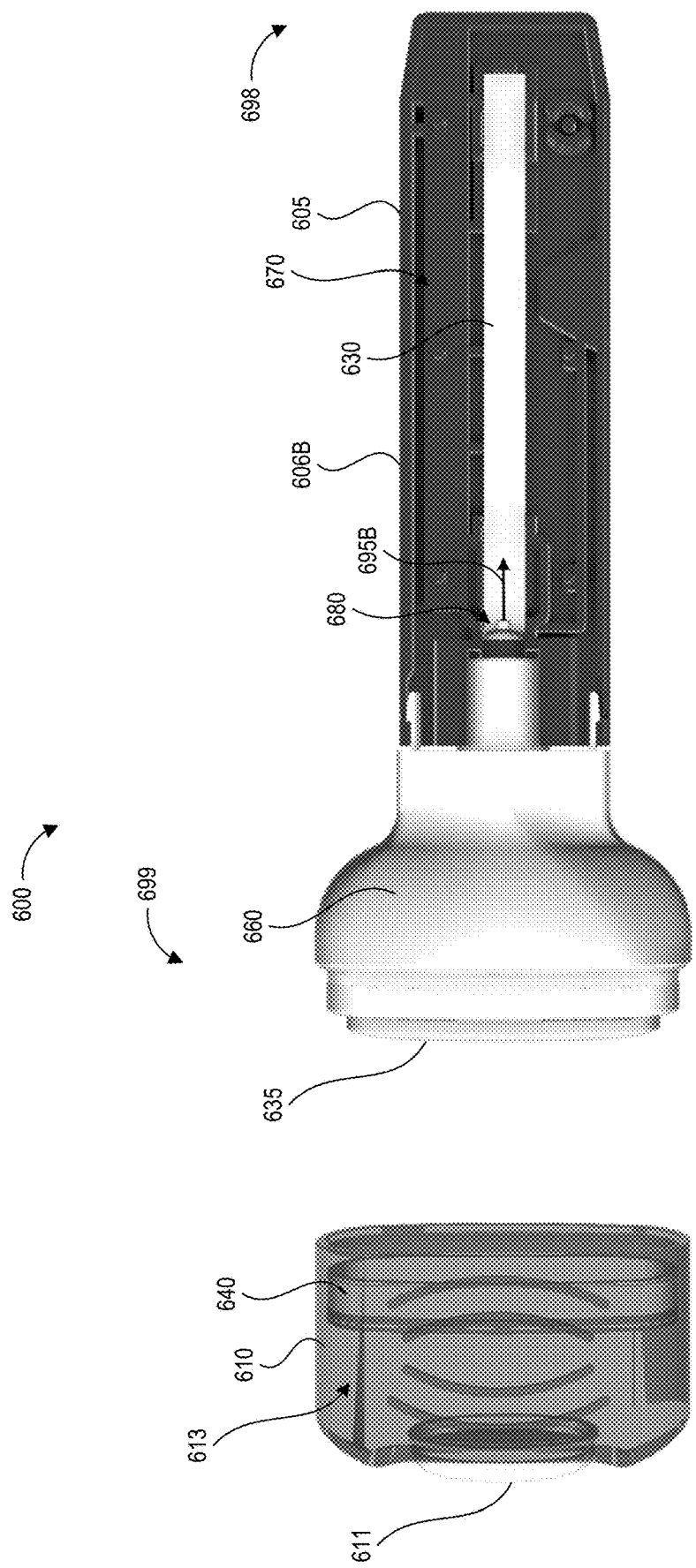

FIG. 6C shows a top view of the collection device 600 without its upper cartridge portion 606A (with only the lower cartridge portion 606B) to reveal the inner components. FIG. 6C also depicts the collection device 600 with the cap 610 removed, illustrating how the swab material 635 extends from the distal end 699 of the elongate body 605. Some embodiments can include a semi-rigid sheet of material within or along a surface the swab material 635, which can assist in sample collection by acting as a squeegee and/or backer that supports the swab material 635. The retaining member 660 couples the swab material 635 to the elongate body 605.

As shown in FIG. 6C, the test strip 630 is housed in an enclosure 670 of the elongate body 605. The enclosure 670 can be considered as the interior cavity of the elongate body 605, formed by interior surfaces of the upper cartridge portion 606A, lower cartridge portion 606B, and retaining member 660. The enclosure 670 can be substantially sealed, for example in a fluid-tight manner, within the elongate body 606. "Substantially sealed" refers to how the enclosure 670 is designed to prevent egress of potentially contaminated fluid from its interior, but still includes the fluid path (a second portion 695B which is depicted in FIGS. 6C and 6E) that allows passage of fluid from the swab material 635 into the enclosure 670 to contact the test strip 630. For example, the enclosure 670 can have a fluid-tight seal along a seam or junction between the upper cartridge portion 606A and lower cartridge portion 606B, and can have a fluid-tight seal along a seam or junction at a distal aperture of the elongate body 605 between the upper cartridge portion 606A, the lower cartridge portion 606B, and the retaining member 660.

Figure 6D:
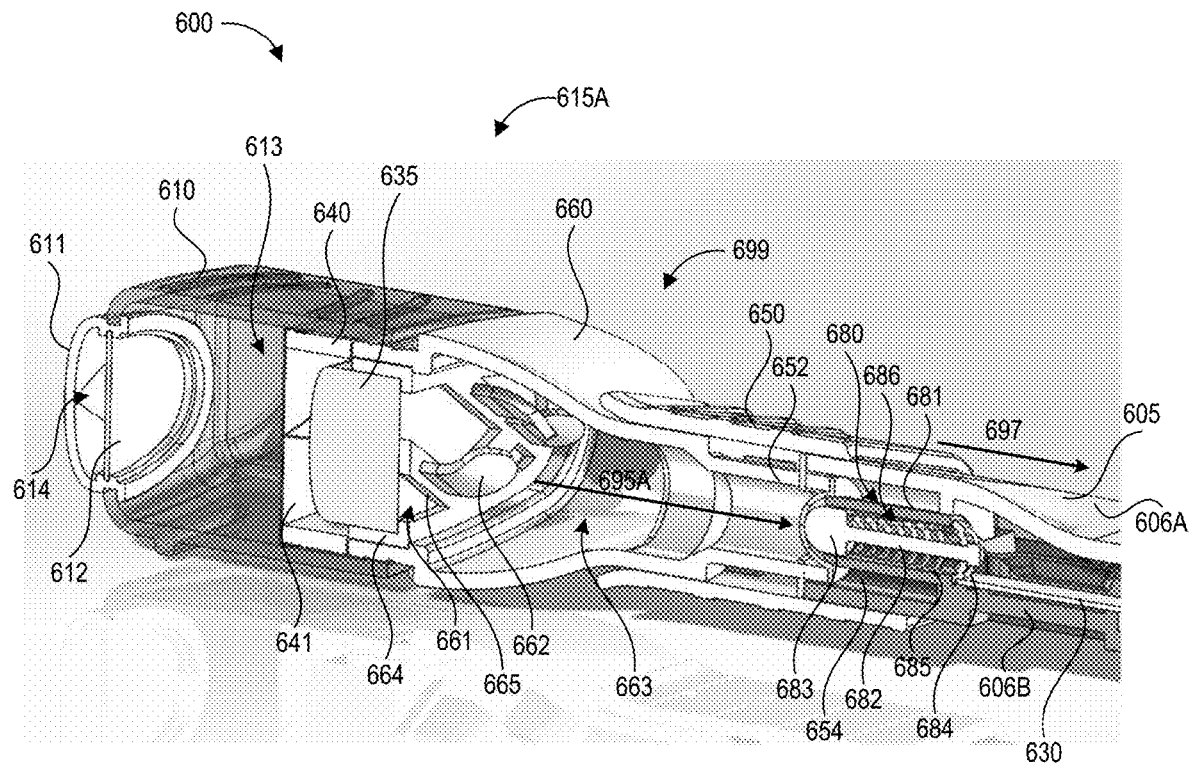
Figure 6E:
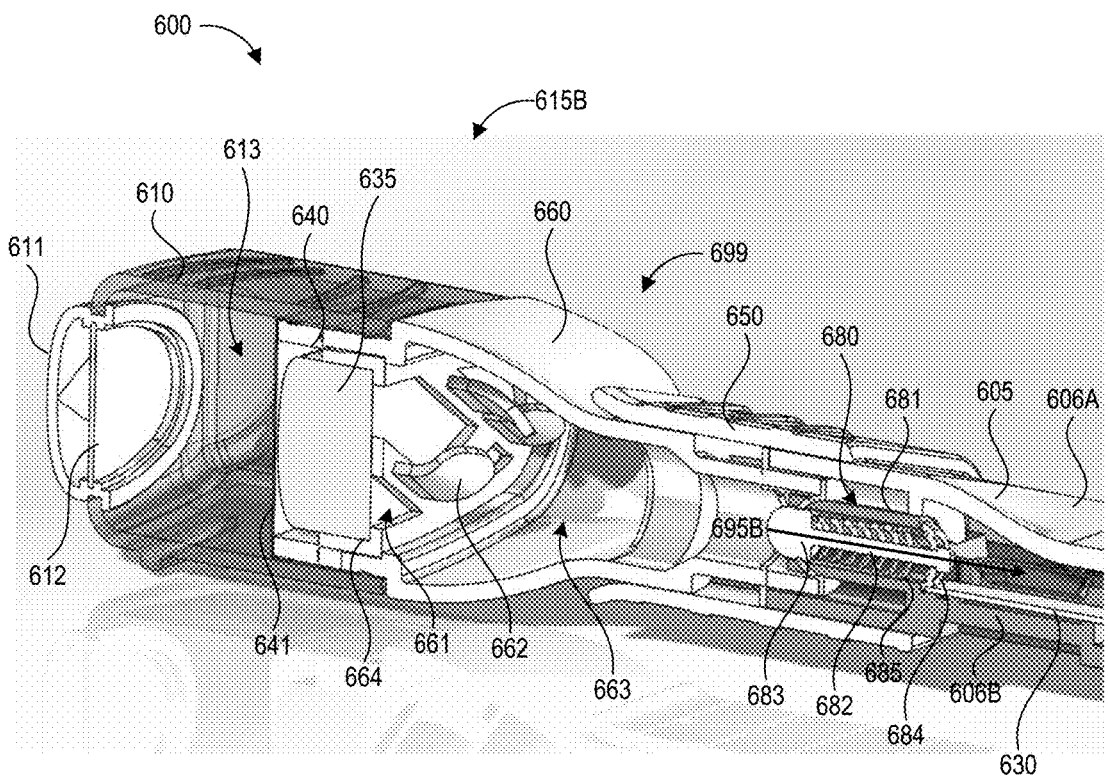

A dosing mechanism 680, described in further detail with respect to FIGS. 6D and 6E, selectively passes fluid eluted from the swab material 635 along the second portion 695B of the fluid path to the test strip 630. The dosing mechanism 680 can be open to receive fluid from the swab material 635 and can seal the second portion 695B of the fluid path in the enclosure 670 when in a "fluid entry" configuration. The dosing mechanism 680 can also seal off (e.g., fluidically isolate) the swab material 635 from the enclosure 670 and open the fluid path into the enclosure 670 when in a "fluid delivery" configuration.

FIG. 6C also depicts the swab receiving member 640 of the cap 610. The swab receiving member 640 is sized and positioned to receive the swab material 635 when the cap 610 is applied to the retaining member 660. A reservoir 613 formed in the cap 610 can hold a liquid, for example a buffer solution designed to promote shedding of collected contaminants from the swab material 635. When a user actuates a pump button 611, this can break a frangible seal 641 (visible in FIGS. 6D and 6E) of the swab receiving member 640, thereby saturating the swab material 635. It will be understood that embodiments of the present disclosure can be implemented with a cap that does not include a swab receiving member and/or reservoir in the cap.

The user may receive the collection device 600 packaged with the cap 610 applied. The swab material 635 can be pre-moistened, for example with a liquid designed to optimize pickup efficiency of the target contaminant from a test surface. The cap 610 can include gasket(s) or other sealing mechanisms to maintain the pre-moistened condition of the swab material 635 prior to use. The user can remove the cap 610 and pass the moistened swab material 635 along the test surface, for example as described above with respect to FIG. 1. After the collection procedure is complete, the user can put the cap 610 back onto the retaining member 660 and activate the pump button 611 to flush any collected contaminants from the swab material 635.

FIG. 6D depicts a cross-sectional view of the distal end 699 of the collection device 600 showing the collar 650 in a first position and the dosing mechanism 680 in the fluid entry configuration, and FIG. 6E depicts a cross-sectional view of the distal end 699 of the collection device 600 showing the dosing mechanism 680 in the fluid delivery configuration.

FIGS. 6D and 6E depict additional details of the cap 610, including a seal 612 in the pump button assembly. The cap 610 also includes the frangible seal 641 positioned between the reservoir 613 and the swab material 635. The pump button 611 can be a deformable material that allows it to be compressed into a pump chamber 614 of the push button assembly, for example by a finger of a user. The user can depress the pump button 611 a number of times to increase the pressure within the reservoir 613, causing the seal 641 to break. The pump button 611 can include vents (e.g., small apertures) to allow air to be drawn into the pump chamber 614 when the pump button 611 is released. The filter 612 can be a gas-permeable, liquid impermeable material to prevent any liquid within the reservoir 613 from being released into the environment of the collection device 600. In some embodiments, the filter 612 can be hydrophobic. The user may depress the pump button 611 an additional number of times to flush fluid through the swab material.

FIGS. 6D and 6E also depict additional details of the retaining member 660. The swab material 635 is retained in a collar 664 of the retaining member 660. The retaining member 660 forms sample receiving bladder 663 on the proximal side of the collar 664 for containing any fluid eluted from the swab material 635 along the first portion 695A of the fluid path between the swab material 635 and the test strip 630. The first portion 695A of the fluid path extends between the proximal side of the swab material 635 and the distal end of the dosing mechanism 680. The collar 664 includes apertures 661 that allow fluid to pass from the swab material 635 into the sample receiving bladder 663. A number of fins 662 are disposed on the proximal surface of the collar 664 along support structures 665 that extend between (and form) the apertures 661. Beneficially, the fins 662 can promote turbulence in fluid eluted from the swab material 635 into the sample receiving bladder 663, mixing the fluid into a homogenous solution.

After depressing the pump button 611 the desired number of times to flush the swab material 635, the sample receiving bladder 663 contains a substantially homogenous solution including any collected contaminants. This solution can be provided to the test strip 630 via the dosing mechanism 680. For example, the user can slide the collar 650 proximally along the elongate body 605 in the direction of arrow 697. This can also cause movement of the retaining member 660 that is coupled to the collar 650 relative to the elongate body 605, where the motion of the retaining member 660 is toward the proximal end 698 of the elongate body 605. A tubular end 652 of the retaining member 660 can slide into a corresponding recess 654 surrounding the dosing mechanism 680, until the collar 650 has transitioned from the first position shown in FIG. 6D to the second position shown in FIG. 6E.

The dosing mechanism 680 can include a tubular body 681 forming an interior lumen 686. A piston 682 can be disposed within the interior lumen 686 for selectively sealing and opening the dosing mechanism. The piston 682 can have an enlarged distal end 683 having a diameter that substantially corresponds to the interior diameter of the interior lumen 686, such that the enlarged distal end 683 can both prevent fluid from entering the distal aperture of the interior lumen 686 and push fluid through the proximal aperture of the interior lumen 686. The piston 682 can have an elongate length extending between the enlarged distal end 683 and a proximal seal 684. The proximal seal 684 can be formed as a dish-shaped member that seals the proximal aperture of the interior lumen 686 when in the configuration shown in FIG. 6D. The piston 682 can be biased in a position that causes the proximal seal 684 to seal the proximal aperture, for example by a spring 685 or other biasing element (e.g., shape memory alloy, magnets).

The enlarged distal end 683 can be spring-loaded and intended to push through a pre-slit valve. The pre-slit valve can be connected to the retaining member 660 assembly as a seal, while the enlarged distal end 683 is part of the cartridge assembly. This action can dose the correct volume (e.g. 75 microliters plus or minus 50-150 microliters, in some implementations) through and onto the strip. The collar 650 can be biased toward the retaining member 660 so that releasing its locking feature and sliding it away from the retaining member 660 would release the assembly of the retaining member 660 from the cartridge. The collar 650 can have connections to the enlarged distal end 683 closer to the proximal seal 684 which can control its movement.

Overview of Example Assay Reader Devices and Operations

Figure 7:
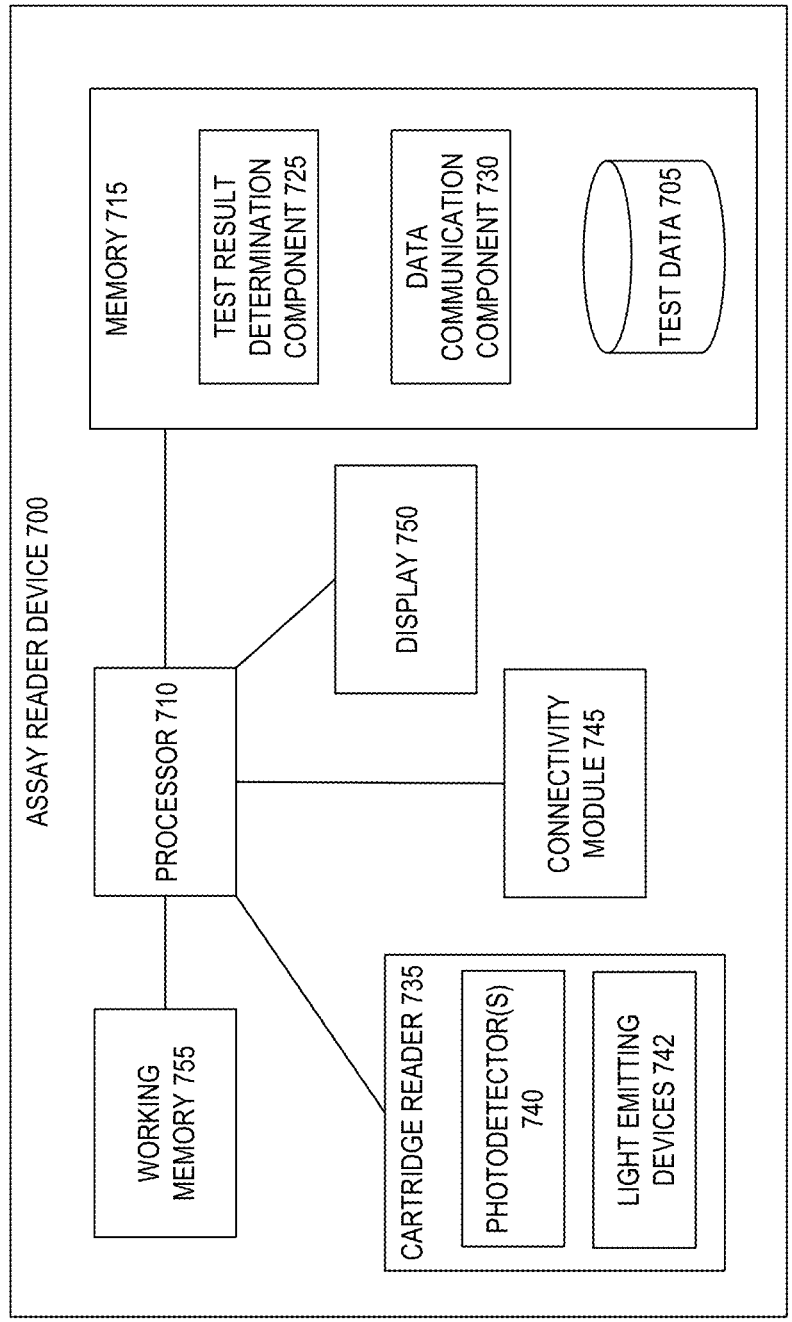
FIG. 7 depicts a high level schematic block diagram of an example reader device that can read the test devices of FIGS. 4A-6E.

FIG. 7 illustrates a schematic block diagram of one possible embodiment of components of an example assay reader device 700. The components can include a processor 710 linked to and in electronic communication with a memory 715, working memory 755, cartridge reader 735, connectivity module interface 745, and display 750.

Connectivity module 745 can include electronic components for wired and/or wireless communications with other devices. For example, connectivity module 745 can include a wireless connection such as a cellular modem, satellite connection, or Wi-Fi, or via a wired connection. Thus, with connectivity module 745 the assay reader device can be capable of sending or uploading data to a remote repository via a network and/or receiving data from the remote repository. As such, the test data of such assay reader devices can be stored and analyzed, alone or in the aggregate, by remote devices or personnel. A module having a cellular or satellite modem provides a built-in mechanism for accessing publicly available networks, such as telephone or cellular networks, to enable direct communication by the assay reader device with network elements or other testing devices to enable electronic test result transmission, storage, analysis and/or dissemination without requiring separate intervention or action by the user of the device. In some embodiments connectivity module 745 can provide connection to a cloud database, for example a server-based data store. The cloud based connectivity module can enable ubiquitous connectivity of assay reader devices without the need for a localized network infrastructure.

The cartridge reader 735 can include one or more photodetectors 740 for reading an assay held in an inserted cartridge and optionally any information on the inserted cartridge, for example a barcode printed on the cartridge, and one or more light emitting devices 742 for illuminating the inserted cartridge at one or more wavelengths of light. The cartridge reader 735 can send image data from the one or more photodetectors to the processor 710 for analysis of the image data representing the imaged assay to determine a test result of the assay. The cartridge reader 735 can further send image data from the one or more photodetectors representing the imaged cartridge for use in determining which one of a number of automated operating processes to implement for imaging the assay and/or analyzing the image data of the assay. The photodetector(s) 740 can be any device suitable for generating electric signals representing incident light, for example a PIN diode or array of PIN diodes, a charge-coupled device (CCD), or a complementary metal oxide semiconductor (CMOS) sensor, to name a few examples. The cartridge reader 735 can also include a component for detecting cartridge insertion, for example a mechanical button, electromagnetic sensor, or other cartridge sensing device. An indication from this component can instruct the processor 710 to begin an automated assay reading process without any further input or instructions from the user of the device 700.

Processor 710 can be configured to perform various processing operations on image data received from the cartridge reader 735 and/or connectivity module interface 745 in order to determine and store test result data, as will be described in more detail below. Processor 710 may be a general purpose processing unit implementing assay analysis functions or a processor specially designed for assay imaging and analysis applications. The processor 710 can be a microcontroller, a microprocessor, or ASIC, to name a few examples, and may comprise a plurality of processors in some embodiments.

As shown, the processor 710 is connected to a memory 715 and a working memory 755. In the illustrated embodiment, the memory 715 stores test result determination component 725, data communication component 730, and test data repository 705. These modules include instructions that configure the processor 710 of device 700 to perform various module interfacing, image processing, and device management tasks. Working memory 755 may be used by processor 710 to store a working set of processor instructions contained in the modules of memory 715. Alternatively, working memory 755 may also be used by processor 710 to store dynamic data created during the operation of device 700.

As mentioned above, the processor 710 may be configured by several modules stored in the memory 715. The test result determination component 725 can include instructions that call subroutines to configure the processor 710 to analyze assay image data received from the photodetector(s) 740 to determine a result of the assay. For example, the processor can compare image data to a number of templates or pre-identified patterns to determine the test result. In some implementations, test result determination component 725 can configure the processor 710 to implement adaptive read processes on image data from the photodetector(s) 740 to improve specificity of test results and to reduce false-positive results by compensating for background and non-specific binding.

The data communication component 730 can determine whether a network connection is available and can manage transmission of test result data to determined personnel and/or remote databases. If the device 700 is not presently part of a network, the data communication component 730 can cause local storage of test results and associated information in the test data repository 705. In some case, the device 700 can be instructed to or automatically transmit the stored test results upon connection to a network. If a local wired or wireless connection is established between the device 700 and another computing device, for example a hospital, clinician, or patient computer, the data communication component 730 can prompt a user of the device 700 to provide a password in order to access the data in the repository 705.

The processor 710 can be configured to control the display 750 to display captured image data, imaged barcodes, test results, and user instructions, for example. The display 750 may include a panel display, for example, a LCD screen, LED screen, or other display technologies, and may implement touch sensitive technologies.

Processor 710 may write data to data repository 705, for example data representing captured images of assays, instructions or information associated with imaged assays, and determined test results. While data repository 705 is represented graphically as a traditional disk device, those with skill in the art would understand that the data repository 705 may be configured as any storage media device. For example, data repository 705 may include a disk drive, such as a hard disk drive, optical disk drive or magneto-optical disk drive, or a solid state memory such as a FLASH memory, RAM, ROM, and/or EEPROM. The data repository 705 can also include multiple memory units, and any one of the memory units may be configured to be within the assay reader device 700, or may be external to the device 700. For example, the data repository 705 may include a ROM memory containing system program instructions stored within the assay reader device 700. The data repository 705 may also include memory cards or high speed memories configured to store captured images which may be removable from the device 700.

Although FIG. 7 depicts a device having separate components to include a processor, cartridge reader, connectivity module, and memory, one skilled in the art would recognize that these separate components may be combined in a variety of ways to achieve particular design objectives. For example, in an alternative embodiment, the memory components may be combined with processor components to save cost and improve performance.

Additionally, although FIG. 7 illustrates a number of memory components, including memory 715 comprising several modules and a separate memory 755 comprising a working memory, one of skill in the art would recognize several embodiments utilizing different memory architectures. For example, a design may utilize ROM or static RAM memory, internal memory of the device, and/or an external memory (e.g., a USB drive) for the storage of processor instructions implementing the modules contained in memory 715. The processor instructions may be loaded into RAM to facilitate execution by the processor 710. For example, working memory 755 may comprise RAM memory, with instructions loaded into working memory 755 before execution by the processor 710.

Overview of Example Networked Testing Environment

Aspects of the present disclosure relate to a contamination test data management system. There are drug preparation systems, surface contamination tests, and healthcare worker safety procedures in the hospital and other healthcare delivery environments. These three areas are connected only to the extent that they have a common goal: to reduce or eliminate healthcare worker exposure to hazardous drugs, and to ensure patients are provided correct drug doses. The described hazardous contamination detection kits, systems and techniques improve upon existing approaches by linking these three areas, sensing patterns and trends, and targeting worker feedback and training. By creating and analyzing associations between data regarding dose preparation, personnel activities, and contamination test results, the disclosed systems can provide information to healthcare workers and management targeted at risk identification, feedback, and training. A beneficial outcome can include behavioral and/or workflow changes to reduce exposure risk in the test areas.

There are several existing solutions for assisting with pharmacy (or other clinical setting) drug preparation workflow. Each of these systems is designed to enhance patient safety through automated preparation or verification steps in compounding drugs. These systems are often used with hazardous drugs, such as chemotherapy agents, because there is little room for error with these drugs due to the health risks of exposure to even trace amounts. One such system performs automated dose calculation, weight-based (gravimetric) preparation and verification, integrated drug and consumable barcode verification, real-time automated documentation of the compounding process, and step-by-step compounding guidance. Other examples can employ a camera that captures images of products used in dose preparation and optionally an integrated weighing scale design with step-by-step guidance and automatic documentation.

While these systems help automate several aspects of drug preparation, they do not address pre- and post-preparation issues in the pharmacy, such as managing data associated with surface contamination testing (for example, floors, walls, hoods, etc.). They also do not manage data associated with air testing, nor data from testing individuals via fingertip, urine, blood or any other personal exposure monitoring.

Surface wipe tests are available from companies such as ChemoGLO™ which provide quantitative analysis of the antineoplastic agents 5-fluorouracil, ifosfamide, cyclophosphamide, docetaxel and paclitaxel. An example existing kit contains enough materials to conduct six surface wipes. The wipes and samples are sent to an outside laboratory, and reports are provided back to the test location within three to four weeks. Such tests and delayed reports are disconnected processes from day to day activities in the pharmacy.

Hazardous drugs, particularly chemotherapy drugs, are known to contaminate surfaces and air in pharmacies and other patient care settings, which presents a significant health risk to pharmacy and other healthcare workers. Further, the United States Pharmacopeia (Cpater 797, 28th Rev) recommends sampling of surfaces for contamination with hazardous drugs at least every six months. With improved testing technology, better feedback and improved outcomes, the frequency of testing is expected to become a more routine activity.

Figure 8:
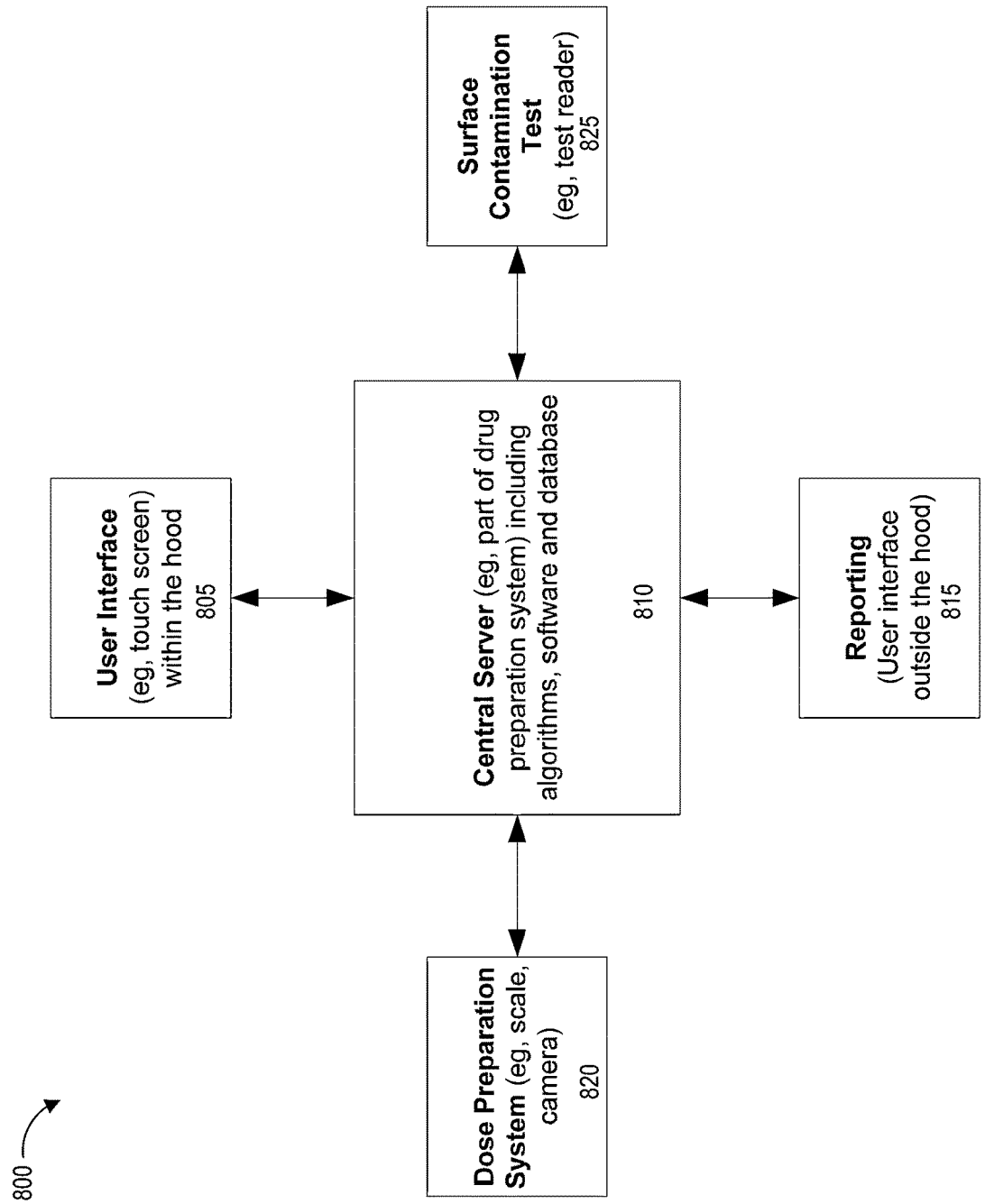
FIG. 8 depicts a high level schematic block diagram of an example networked test system environment that can include the reader device of FIG. 7.

FIG. 8 depicts a high level schematic block diagram of an example networked test system environment 800. Hazardous contamination detection kits described herein can be used in the networked test system environment 800 to improve contamination detectin, risk identification, feedback, and training. The networked environment 800 includes a user interface 805, dose preparation system 820, surface contamination test 825, and reporting system 815 in network communication with a central server 810 (and/or one another) via a network. The network can be any suitable data transfer network or combination of networks including wired networks and/or wireless networks such as a cellular or other publicly accessible network, WiFi, and the like.

The user interface 805 supports system interaction by the test operator and can be located in the work area, for example in or near the testing environment. This facilitates interaction without the test operator having to remove and reapply personal safety equipment in order to use the system.

The dose preparation system 820 can be hardware associated with a gravimetric dose preparation system, a scale, robotics, or devices that are designed to assist in the preparation of safe drug doses for the patient.

The surface contamination test 825 can include a local test processing system which is in network communication with at least the central server 810. For example, the local test processing system can be the assay reader device 800 of FIG. 8.

Central server 810 can implement the algorithms, decisions, rules, and heuristics involved with management of contaminant testing data, and can store data (individual and aggregate), handle data input and/or output, generate reports, provide the user interface, and the like. Though referred to as a central server, these functions could be carried out in a distributed fashion, virtually, in any location.

The reporting user interface 815 can provide raw and processed data to the user or safety manager regarding the relationship between activities in the pharmacy and test results.

In some implementations, the above descriptions apply to tests that are performed immediately in a pharmacy, hospital, or other clinical setting. However, the described testing is not limited to architectures where instant, immediate, or real-time connectivity is available. For example, if a local wipe test processing system is not available, data from a remote system can be transmitted to the central server using any number of methods. Results from tests may be fed in to an interface manually, electronically encoded, or in machine readable format. Data networks (e.g., internet, wireless, virtual private, cloud-based) can be used to input data from a remote lab (outside the pharmacy, hospital, or clinic) that performs testing either immediately or at a later time. The main difference between immediate local contamination detection versus remote testing is a potential time delay. As described above, current contaminant detection occurs in a two-step process with the steps performed at different locations. First, collection happens at site of possible contamination. Collection occurs a time A. Second, detection of the contamination occurs in a laboratory facility geographically separate from the contamination. Detection occurs at a time B, which is weeks or even months after collection occurred. The present disclosure provides a system including collection device and detection device in one kit. Using the disclosed kit, collection and detection occur at the site of possible contamination, and detection occurs within minutes of collection. For example, collected fluid can be provided onto an assay immediately (for example, within seconds such as but not limited to within 1, 2, 3, 4, 5, 10, or 15 seconds) after agitation of the fluid within a container as described herein. The collected fluid can be provided to the assay for up to 3 hours (360 minutes) after agitation in some embodiments. In some embodiments, instructions for use include a recommendation to the user not to apply the collected fluid to the assay more than 3 hours after collection because accuracy may decrease after 3 hours. After the fluid is added to the assay it can take around five minutes to fully develop in some non-limiting examples. In one advantageous implementation, the assay is read by a detection system around the time of its complete development. As such, the disclosed kits can provide test results indicating the presence, absence, and/or degree of contamination between 2-365 minutes after completion of sample collection, in some embodiments. Laboratory testing of embodiments of test kits described herein has demonstrated that reliable results can be obtained within about 5 minutes of completion of sample collection, and in some cases in as little as 2 minutes of completion of sample collection. This represents a dramatic improvement in the time to obtain a test result indicating the presence, absence, and/or degree of contamination of a hazardous drug over prior systems.

Embodiments of the system 800 described herein directly link activities performed in the test environment to test results. For example, the system 800 can directly link contaminant test results to when activities (for example, during antineoplastic drug preparation, dosing, and the like) were performed, who performed these activities (for example, through authentication), where the activities occurred (which hood, nearby floor, air test), and other events (such as spills, wasting of materials, or improper waste disposal) which can be manually or automatically recorded. In some embodiments, the central server 810 can perform analysis of the related information to identify trends in hazardous contamination levels, and can output recommendations for preventing or mitigating hazardous contamination levels in certain areas.

Figure 9:
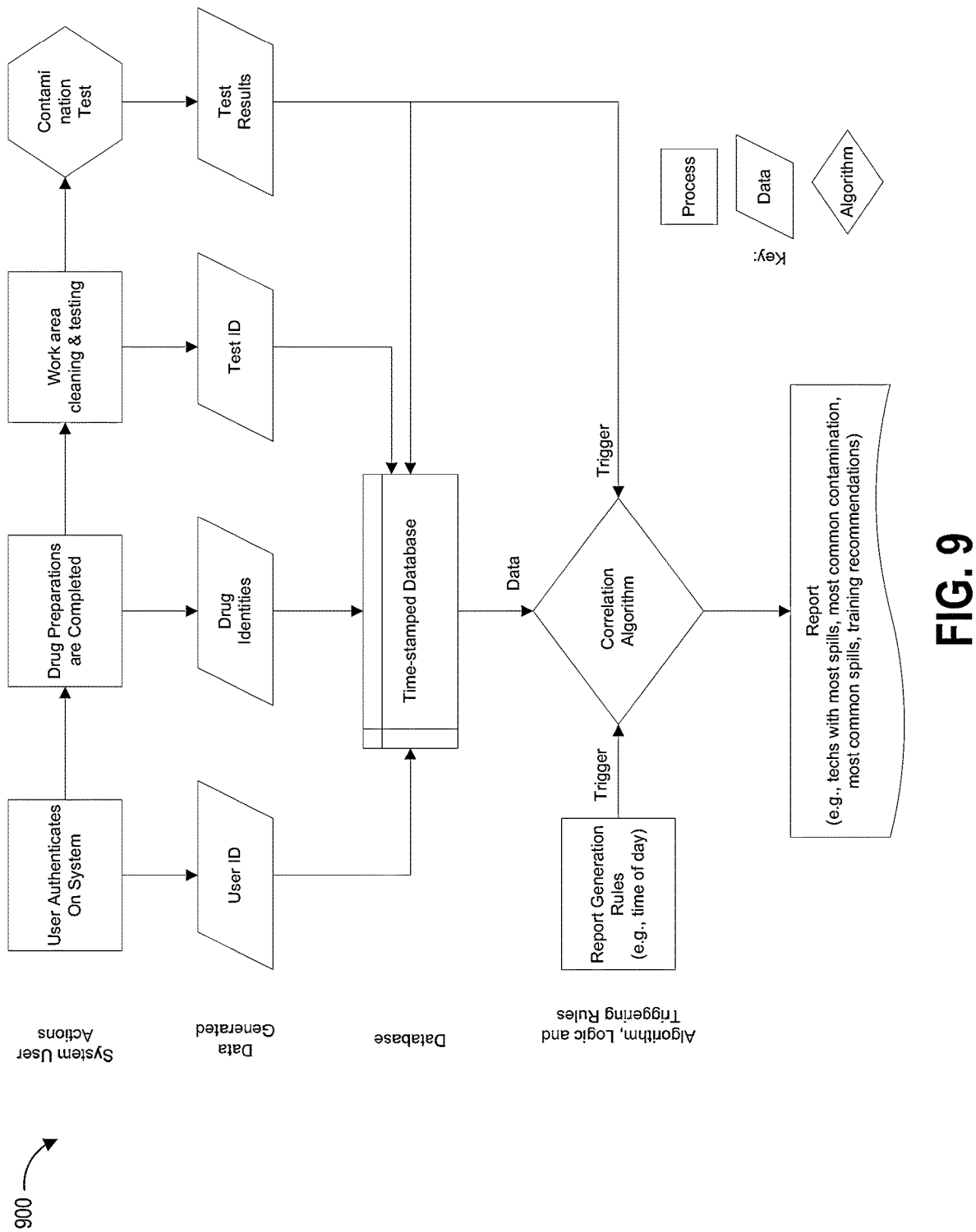
FIG. 9 depicts a flow chart of an example process for test data generation, analysis, and reporting using the collection devices and reader devices described herein.

FIG. 9 depicts a flow chart of an example process 900 for test data generation, analysis, and reporting that can be implemented in some embodiments of the system 800 of FIG. 8.

The dose preparation system 820, whether volumetric, gravimetric, photographic, or bar code scanning, can be capable of keeping a record of every dose that was prepared in a particular pharmacy hood or other work area or clinical care area, when the dose was prepared and/or administered, and who prepared and/or administered the dose (for example, the identity of the pharmacy technician). As described above, this information can be correlated with the results of the contamination test.

The correlation algorithm can, in some embodiments, match detected contamination with specific personnel who might have created or contributed to the contamination. For example, if three technicians worked in a hood, and only one worked with compound x, and compound x was identified in a contamination test, then the technician who worked with compound x might be targeted for training or follow up testing.

The correlation algorithm can, in some embodiments, provide contamination test guidance by limiting tests to compounds that were actually used over a period of time, or used since the last contamination test. In a scenario where more than one test is required to screen for multiple possible contaminants, the cost may increase for a number of reasons. For example, it may take a longer period of time to perform testing due to more samples being needed. The time it takes to run a test may be longer. Sample preparation may be more complex. Each test may have an incremental cost, so tailoring tests may lower the overall cost. Advantageously, the dose preparation system could direct the user, or an automated system, to perform only contamination tests for drugs that were prepared in a specific location or hood.

The correlation algorithm can, in some embodiments, improve the specificity of contamination tests by utilizing a priori knowledge of drugs that were prepared in the hood. For example, if a contamination test shows a positive result, but is not capable of indicating which of a family of possible contaminants actually has been identified, the database of drugs prepared in the hood could be queried for all of those possible drugs, and the test result narrowed to the ones actually prepared. In some implementations, further testing can be performed for those specific drugs.

The correlation algorithm can, in some embodiments, determine systematic issues with devices used in preparing drugs. Drug preparation systems can have the capability to store information representing the products and devices used in drug preparation. For example, information on syringe types (manufacturer, volume etc.), closed system transfer devices, connectors, spikes, filters, needles, vials, and IV bags, to name a few examples, can be stored along with the drug and diluent data in the preparation systems database. Failures can be linked to specific devices and directly help with risk mitigation.

The correlation algorithm can, in some embodiments, identify drug manufacturers, dose and containers that systematically fail, resulting in detected contamination. The correlation algorithm can identify procedures that commonly cause contamination, such as reconstitution steps.

The system 800 can provide some or all of these analytics, alone or in combination, in various embodiments.

The system 800 can be designed to implement workflows that are initiated based on a set of conditions. For example, one condition that can trigger a workflow is the detection of contamination. Examples of workflows are described below.

A decontamination workflow can include the following procedures. The system 800 can instruct a user how to contain and decontaminate a specific area, depending on what area the test was performed in. Instructions can include audio, text, video, and the like. After decontamination, the workflow can continue to instructions on performing repeat contamination tests to ensure the area was properly decontaminated. If testing fails again, the decontamination procedure can be repeated.

The system 800 can be configured to provide instructions through the user interface 805 and/or dose preparation system 820 (or any other means of communication, including printed instructions, other displays, voice output and input, direct messages to designated users, etc.). These instructions can be configured to be specific for certain sources of contaminants.

Another example workflow is repeat testing of the area of contamination, prior to decontamination. This may be a useful workflow if the specificity of a particular test is not high. The objective could be to re-test with the same test, or perform further tests to identify more specifically, what the source and/or level of contamination is. A follow-on step could be specific decontamination instructions, already described above.

In various workflows, system 800 can be configured to receive, prompt, and/or wait for input during the workflow to acknowledge completion of each step. The system 800 can be configured to capture decontamination procedure evidence, such as photographic, video, audio, proximity information for future review, training, documentation, and the like.

System 800 can be configured to identify risks from preparation issues. For example, the system 800 can analyze data already captured by a drug preparation system, or provide means to capture data regarding drug preparation issues, problems or errors. For example, when material is wasted, the user involved can be questioned about whether there was a spill or any surface contamination that caused the wasting. System 800 can link wasting with positive contamination tests, if wasting is commonly caused by spills.

System 800 can be adapted for use in non-pharmacy healthcare environments including, but not limited to, hospitals, clinics, hospice environments, and veterinary treatment centers. The system 800 can be adapted to other areas of patient care, such as the patient floor, nursing, drug delivery (e.g., infusion, injection), patient room, bathroom, etc. Contamination tests can be performed in any of these settings, and this data can be fed back to the system 800. As described above, detected contamination can be correlated with personnel, protocols followed, specific drugs, devices, locations, and any other parameter of interest. Any parameter around the delivery of drugs that can be encoded can be correlated with the presence of contamination to provide feedback to risk managers, clinical and pharmacy personnel. Further, dose preparation and dispensing can occur in many locations outside the pharmacy, and similar workflows can be employed in those areas, including remote contamination test preparation and execution.

The physical location of specific functions performed by the system 800 are not restricted to the pharmacy or hospital data center. Any structure or function of the system 800, including the database, correlation and analysis, data entry, data display, reporting, etc., can be carried out in any system in any location. A system model may be to have a central web-based service, for example. Another model may be to have remote reporting and notification capability through remote devices like smart phones, pagers, computers, displays, applications etc.

Supply of devices can be automated through any of the previously described systems. For example, pharmacies may be provided resupply of test kits by system 800, and such resupply can be automated in some embodiments by managing an inventory of kits and initiating a resupply when stock falls below a certain level.

Implementing Systems and Terminology

Implementations disclosed herein provide systems, methods and apparatus for detection of the presence and/or quantity of antineoplastic agents or other environmental contaminants. One skilled in the art will recognize that these embodiments may be implemented in hardware or a combination of hardware and software and/or firmware.

The assay reader device may include one or more image sensors, one or more image signal processors, and a memory including instructions or modules for carrying out the processes discussed above. The device may also have data, a processor loading instructions and/or data from memory, one or more communication interfaces, one or more input devices, one or more output devices such as a display device and a power source/interface. The device may additionally include a transmitter and a receiver. The transmitter and receiver may be jointly referred to as a transceiver. The transceiver may be coupled to one or more antennas for transmitting and/or receiving wireless signals.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. The term "computer-program product" refers to a computing device or processor in combination with code or instructions (e.g., a "program") that may be executed, processed or computed by the computing device or processor. As used herein, the term "code" may refer to software, instructions, code or data that is/are executable by a computing device or processor.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component or directly connected to the second component. As used herein, the term "plurality" denotes two or more. For example, a plurality of components indicates two or more components.

The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like. The phrase "based on" does not mean "based only on," unless expressly specified otherwise. In other words, the phrase "based on" describes both "based only on" and "based at least on."

The previous description of the disclosed implementations is provided to enable any person skilled in the art to make or use implementations of the present disclosure. Various modifications to these implementations will be readily apparent to those skilled in the art, and the generic principles defined herein may be applied to other implementations without departing from the scope of the present disclosure. Thus, the present disclosure is not intended to be limited to the implementations shown herein but is to be accorded the widest scope consistent with the principles and novel features disclosed herein.

What is claimed is:

1. A hazardous contaminant test system comprising:
   a collection device comprising:
   an elongate body forming an enclosure,
   an assay test strip disposed within the enclosure, the assay test strip comprising a reaction zone configured to indicate the presence of a hazardous contaminant,
   an absorbent swab material coupled to a distal end of the elongate body, wherein the absorbent swab material is configured to absorb a first fluid from a test surface, wherein the first fluid is configured to lift the hazardous contaminant from the test surface,
   a fluid pathway positioned between the absorbent swab material and the assay test strip, and
   a cap configured to seal the distal end of the elongate body, wherein the cap comprises a second fluid configured to flush the hazardous contaminant from the absorbent swab material, wherein when the cap is applied to the elongate body in a first orientation the distal end of the elongate body is prevented from releasing the second fluid, and wherein when the cap is applied to the elongate body in a second orientation the elongate body causes the second fluid to be released.

2. The hazardous contaminant test system of claim 1, wherein the cap further comprises a reservoir containing the second fluid.

3. The hazardous contaminant test system of claim 2, wherein the cap further comprises a frangible seal positioned between the reservoir and the distal end of the elongate body when the cap is applied to the elongate body.

4. The hazardous contaminant test system of claim 3, wherein the cap further comprises a pump that, when activated, opens the frangible seal to release the second fluid into the absorbent swab material.

5. The hazardous contaminant test system of claim 3, wherein the absorbent swab material is configured to break the frangible seal when the cap is applied to the elongate body in the second orientation.

6. The hazardous contaminant test system of claim 3, wherein the cap further comprises a swab receiving member coupled to the frangible seal.

7. The hazardous contaminant test system of claim 6, wherein the swab receiving member is configured such that the absorbent swab material does not enter the swab receiving member when the cap is applied to the elongate body in the first orientation and such that the absorbent swab material enters the swab receiving member when the cap is applied to the elongate body in the second orientation, and wherein the absorbent swab material is configured to break the frangible seal when the cap is applied to the elongate body in the second orientation.

8. A hazardous contaminant collection device comprising:
   an elongate body forming an enclosure;
   an assay test strip disposed within the enclosure, the assay test strip comprising a reaction zone configured to indicate the presence of a hazardous contaminant;
   an absorbent swab material coupled to a distal end of the elongate body, wherein the absorbent swab material is configured to lift the hazardous contaminant from a test surface; and
   a cap configured to seal the distal end of the elongate body, wherein the cap comprises a fluid configured to flush the hazardous contaminant from the absorbent swab material, wherein when the cap is applied to the elongate body in a first orientation the distal end of the elongate body is prevented from releasing the fluid, and wherein when the cap is applied to the elongate body in a second orientation the elongate body causes the fluid to be released.

9. The hazardous contaminant collection device of claim 8, wherein the absorbent swab material has a fluid thereon or therein configured to lift the hazardous contaminant from a test surface.

10. The hazardous contaminant collection device of claim 8, wherein the cap further comprises a reservoir containing the fluid.

11. The hazardous contaminant collection device of claim 10, wherein the cap further comprises a frangible seal positioned between the reservoir and the distal end of the elongate body when the cap is applied to the elongate body.

12. The hazardous contaminant collection device of claim 11, wherein the cap further comprises a pump that, when activated, opens the frangible seal to release the fluid into the absorbent swab material.

13. The hazardous contaminant collection device of claim 11, wherein the absorbent swab material is configured to break the frangible seal when the cap is applied to the elongate body in the second orientation.

14. The hazardous contaminant collection device of claim 11, wherein the cap further comprises a swab receiving member coupled to the frangible seal.

15. The hazardous contaminant collection device of claim 14, wherein the swab receiving member is configured such that the absorbent swab material does not enter the swab receiving member when the cap is applied to the elongate body in the first orientation and such that the absorbent swab material enters the swab receiving member when the cap is applied to the elongate body in the second orientation, and wherein the absorbent swab material is configured to break the frangible seal when the cap is applied to the elongate body in the second orientation.

16. A method of testing a test surface for the presence of a hazardous contaminant, the method comprising:
   removing a cap in a first orientation from an elongate body of a collection device to expose an absorbent swab material coupled to an end of the elongate body, the absorbent swab material configured to absorb a first fluid from the test surface, wherein the first fluid is configured to lift the hazardous contaminant from the test surface;
   wiping the test surface with the absorbent swab material to collect the hazardous contaminant from the test surface;
   reapplying the cap to the elongate body in a second orientation to seal the absorbent swab material to isolate the collected hazardous contaminant within the collection device, wherein the cap further comprises a second fluid; and
   releasing the second fluid into the absorbent swab material by pushing the cap onto the elongate body in an orientation in which the absorbent swab material pushes against and opens a frangible seal, wherein when the cap is applied to the elongate body in the first orientation the end of the elongate body is prevented from releasing the second fluid, and wherein when the cap is applied to the elongate body in the second orientation the elongate body causes the second fluid to be released.

17. The method of claim 16, further comprising transferring a volume of liquid from the absorbent swab material to an assay test strip via a fluid-tight path within the collection device, wherein the assay test strip is sealed within the collection device.

18. The method of claim 17, further comprising inserting the assay test strip into an assay reader device.

19. The method of claim 18, further comprising, based on an output of the assay reader device, identifying that the hazardous contaminant is present on the test surface.

20. The method of claim 16, further comprising activating a pump mechanism of the cap to release the second fluid into the absorbent swab material.

\* \* \* \* \*